US008129167B2

(12) United States Patent
Cosman

(10) Patent No.: US 8,129,167 B2
(45) Date of Patent: Mar. 6, 2012

(54) UL16 BINDING PROTEIN 4

(75) Inventor: David J. Cosman, Bainbridge Island, WA (US)

(73) Assignee: Immunex Corporation, Thousand Oaks, CA (US)

( * ) Notice: Subject to any disclaimer, the term of this patent is extended or adjusted under 35 U.S.C. 154(b) by 258 days.

(21) Appl. No.: 12/479,543

(22) Filed: Jun. 5, 2009

(65) Prior Publication Data

US 2009/0274699 A1     Nov. 5, 2009

Related U.S. Application Data

(62) Division of application No. 10/265,811, filed on Oct. 4, 2002, now Pat. No. 7,563,450.

(60) Provisional application No. 60/327,252, filed on Oct. 4, 2001.

(51) Int. Cl.
*C12N 1/00* (2006.01)
*C12N 1/20* (2006.01)
*C12N 15/00* (2006.01)
*C07H 21/04* (2006.01)
*C07K 14/00* (2006.01)
*C07K 16/00* (2006.01)

(52) U.S. Cl. ................. 435/252.3; 435/320.1; 536/23.4; 536/23.5

(58) Field of Classification Search ........................ None
See application file for complete search history.

(56) References Cited

U.S. PATENT DOCUMENTS

| | | | |
|---|---|---|---|
| 6,458,350 B1 | 10/2002 | Cosman et al. | |
| 6,821,522 B2 | 11/2004 | Raulet et al. | |
| 2003/0004311 A1 | 1/2003 | Baker et al. | |
| 2003/0022239 A1 | 1/2003 | Baker et al. | |
| 2004/0219521 A1* | 11/2004 | Tang et al. | 435/6 |
| 2005/0074754 A1 | 4/2005 | Okubo et al. | |

FOREIGN PATENT DOCUMENTS

| | | |
|---|---|---|
| WO | WO 99/31236 A2 | 6/1999 |
| WO | WO 01/07611 A2 | 2/2001 |
| WO | WO 01/40466 A2 | 6/2001 |
| WO | WO 01/49728 A2 | 7/2001 |
| WO | WO 01/71005 A3 | 9/2001 |
| WO | WO 01/83545 A1 | 11/2001 |
| WO | WO 02/068615 A2 | 9/2002 |
| WO | WO 03/014322 A2 | 2/2003 |
| WO | WO 03/054152 | 7/2003 |
| WO | WO 03/074556 | 9/2003 |
| WO | WO 2004/022706 | 3/2004 |

OTHER PUBLICATIONS

Apeler, H. et al., "Expression of natural and synthetic genes encoding herpes simplex virus 1 protease in *Escherichia coli* and purification of the protein," *Eur J Biochem*, 247(3):890-895, 1997.

Azimi, N. et al., "Immunostimulation by induced expression of NKG2D and its MIC ligands in HTLV-1-associated neurologic disease," *Immunogenet*, 58:252-258, 2006.
Bauer, S. et al., "Activation of NK cells and T cells by NKG2D, a receptor for stress-inducible MICA," *Science* 285:727-729, 1999.
Bowie et al., "Deciphering the message in protein sequences: tolerance to amino acid substitutions," *Science* 247:1306-1310, 1990.
Borchers, M.T. et al., "NKG2D ligands are expressed on stressed human airway epithelial cells," *Am J Physiol Lung Cell Mol Physiol*, 291:L222-L231, 2006.
Bork, P., "Powers and pitfalls in sequence analysis: the 70% hurdle," *Genome Research* 10.398-400, 2000.
Burgess et al., "Possible dissociation of the heparin-binding and mitogenic activities of heparin-binding (acidic fibroblast) growth factor-1 from its receptor-binding activities by site-directed mutagenesis of a single lysine residue," *J Cell Biol* 111(5):2129-2138, 1990.
Cao and He, "UL16 binding proteins," *Immunobiol*, 209:283-290, 2004.
Cerboni, C. et al., "Antigen-activated human T lymphocytes express cell-surface NKG2D ligands via an ATM/ATR-dependent mechanism and become susceptible to autologous NK-cell lysis," *Blood*, 10(2):606-614, 2007.
Cerwenka, A. et al., "Ectopic expression of retinoic acid early inducible-1 gene (RAE-1) permits natural killer cell-mediated rejection of a MHC class I-bearing tumor in vivo," *PNAS* 98(20):11521-11526, 2001.
Cerwenka, A. et al., "Retinoic acid early inducible genes define a ligand family for the activating NKG2D receptor in mice," *Immunity* 12:721-727, 2000.
Chalupny, J.N. et al., "ULBP4 is a novel ligand for human NKG2D," *Biochem Biophys Res Commun*, 305(1):129-135, 2003.
Chiorean, E.G. and Miller, J.S., "The biology of natural killer cells and implications for therapy of human disease," *J Hematother Stem Cell Res*, 10:451-463, 2001.
Colucci, F. et al., "Functional dichotomy in natural killer cell signaling: vav1-dependent and -independent mechanisms," *J Exp Med* 193(12):1413-1424, 2001.
Conejo-Garcia et al., "Letal, a tumor-associated NKG2D immunoreceptor ligand, induces activation and expansion of effector immune cells," *Cancer Biol. Ther*. 2(4):446-451, 2003.
Conejo-Garcia et al., "Ovarian carcinoma expresses the NKG2D ligand Letal and promotes the survival and expansion of CD28⁻antitumor T cells," *Cancer Res*. 64:2175-2182, 2004. Cosman, D. et al., The ULBP family of ligands for the NKG2D/DAP10 Receptor, 7th Annual Mtg. Of the Society for National Immunity and 19th Intl. Natural Killer Cell Workshop, San Juan, Puerto Rico, Oct. 7-9, 2001.
Cosman, D. et al., "ULBPs, novel MHC class I-related molecules, bind to CMV glycoprotein UL16 and stimulate NK cytotoxicity through the NKG2D receptor," *Immunity* 14(2):123-133, 2001.
Das, H. et al., "MICA engagement by human Vγ2Vδ2 T cells enhance their antigen-dependent effector function," *Immunity* 15(1): 83-93, 2001.
Déchanet, J. et al., "Implication of γδ T cells in the human immune response to cytomegalovirus," *J Clin Invest*, 103(10):1437-1449, 1999.

(Continued)

*Primary Examiner* — G. R. Ewoldt
*Assistant Examiner* — Marianne Dibrino
(74) *Attorney, Agent, or Firm* — Susan E. Lingenfelter

(57) ABSTRACT

ULBP4, a novel member of the ULBP family has been isolated and characterized. ULBP4 is a useful activator of immune effector cells, particularly of NK cells. Nucleic acids encoding ULBP4, vectors, and cells encoding the same are provided.

6 Claims, 4 Drawing Sheets

OTHER PUBLICATIONS

Depatie, C. et al., Assessment of Cmv1 candidates by genetic mapping and in vivo antibody depletion of NK cell subsets, *Int Immunol*, 11(9):1541-1551, 1999.

Diefenbach, A. et al., "Rae1 and H60 ligands of the NKG2D receptor stimulate tumour immunity," *Nature* 413:165-171, 2001.

Diefenbach, A. et al., "Ligands for the murine NKG2D receptor: expression by tumor cells and activation of NK cells and macrophages," *Nature Immunol* 1(2):119-126, 2000.

Diefenbach, A. et al., "A novel ligand for the NKG2D receptor activates NK cells and macrophages and induces tumor immunity," *Eur. J. Inununol*. 33:381-391, 2003.

Dorfman, D. et al., "In vivo expression of B7-1 and B7-2 by follicular lymphoma cells can prevent induction of T-cell energy but is insufficient to induce significant T-cell proliferation," *Blood* 90(11):4297-4306, 1997.

Doubrovina, E.S. et al., "Evasion from NK cell immunity by MHC class I chain-related molecules expressing colon adenocarcinoma," *J Immunol*, 171:6891-6899, 2003.

Eagle, R.A. et al., "Regulation of NKG2D ligand gene expression," *Hum Immunol*, 67.159-169, 2006.

Gattei, V. et al., "CD30 ligand is frequently expressed in human hematopoietic malignancies of myeloid and lymphoid origin," *Blood* 89(6):2048-2059, 1997.

Gillies, S.D. et al., "Improved circulating half-life and efficacy of an antibody-interleukin 2 immunocytokine based on reduced intracellular proteolysis," *Clin Cancer Res*, 8:210-216, 2002.

Gillics, S.D. et al., "Improving the efficacy of antibody-interleukin 2 fusion proteins by reducing their interaction with Fc receptors," *Cancer Res*. 59(9):2159-2166, 1999.

Gillies, S.D. et al., "Bi-functional cytokine fusion proteins for gene therapy and antibody-targeted treatment of cancer," *Cancer Immunol Immunother*, 51:449-460, 2002.

Girardi, M. et al., "Regulation of cutaneous malignancy by γδ T cells," *Science* 294:605-609, 2001.

Groh, V. et al., "Tumour-derived soluble MIC ligands impair expression of NKG2D and T-cell activation," *Nature*, 419:734-738, 2002.

Hackett, N.R. et al., "Antivector and antitransgene host responses in gene therapy," *Curr Opin Mol Ther*, 2(4):376-382, 2000.

Ho, E.L. et al., "Murine *Nkg2d* and *Cd94* are clustered within the natural killer complex and are expressed independently in natural killer cells," *Proc Natl Acad Sci*USA, 95:6320-6325, 1998.

Holden, S.A. et al., "Augmentation of antitumor activity of an antibody-interleukin 2 immunocytokine with chemotherapeutic agents," *Clin Cancer Res* 7:2862-2869, 2001.

Holmes, M.A. et al., "Structural studies of allelic diversity of the MHC class I homolog MIC-B, a stress-inducible ligand for the activating immunoreceptor NKG2D," *J Immunol* 169:1395-1400, 2002.

Kubin, M. et al., "ULBP1, 2, 3: novel MHC class I-related molecules that bind to human cytomegalovirus glycoprotein UL16, activate NK cells," *Eur J Immunol* 31:1428-1437, 2001.

Kubin, M. et al., "Molecular cloning and biological characterization of NK cell activation-inducing ligand, a counterstructure for CD48," *Eur J Immunol* 29:3466-3477, 1999.

Lanier, L.L., "NK cell receptors," *Annu Rev Immunol*, 16359-393, 1998.

Lazar et al., "Transforming growth factor alpha: mutation of aspartic acid 47 and leucine 48 results in different biological activities," *Mol Cell Biol* 8:1247-1252, 1988.

Li, P. et al., "Crystal structures of RAE-1β and its complex with the activating immunoreceptor NKG2D," *Immunity*, 16:77-86, 2002.

Li, P. et al., "Complex structure of the activating immunoreceptor NKG2D and its MHC class I-like ligand MICA," *Nat Immunol*, 2(5):443-451, 2001.

Lilienfeld, B.G. et al., "Porcine UL16-binding protein 1 expressed on the surface of endothelial cells triggers human NK cytotoxicity through NKG2D," *J Immunol*, 177:2146-2152, 2006.

Lopez-Botet, M. et al., "NK cell recognition of non-classical HLA class I molecules," *Semin Immunol*, 12(2):109-119, 2000.

Lopez-Botet, M. et al., Paired inhibitory and triggering NK cell receptors for HLA class I molecules, *Hum Immunol*, 61(1):7-17, 2000.

Lotze, M.T. et al., "Workshop on cancer biometrics: Identifying biomarkers and surrogates of cancer in patients," *J Immunother*, 28(2):79-119, 2005.

Luo, D. et al., "Rat hepatic natural killer cells (pit cells) express mRNA and protein similar to in vitro interleukin-2 activated spleen natural killer cells," *Cell Immunol* 210:41-48, 2001.

Manilay, J. and Sykes, M., "Natural killer cells and their role in graft rejection," *Curr Opin Immunol*, 10(5):532-538, 1998.

Miller, J., "The biology of natural killer cells in cancer, infection, and pregnancy," *Exp Hematol* 29:1157-1168, 2001.

Moretta, A. et al., "Activating receptors and coreceptors involved in human natural killer cell-mediated cytolysis," *Annu Rev Immunol*, 19:197-223, 2001.

Myers, D. and Uckun, F., "An anti-CD72 immunotoxin against therapy-refractory B-lineage acute lymphoblastic leukemia," *Leukemia and Lymphoma* 18:119-122, Harwood Academic Publishers GmbH, Printed in Singapore, 1995.

Ogasawara, K. et al., "Function of NKG2D in natural killer cell-mediated rejection of mouse bone marrow grafts," *Nature Immunology*, 6(9):938-945, 2005.

Onda, H. et al., "A novel secreted tumor antigen with a glycosylphosphatidylinositol-anchored structure ubiquitously expressed in human cancers," *Biochem Biophys Res Comm* 285(2):235-243, 2001.

Pardoll, D., "Stress, NK receptors, and immune surveillance," *Sci*, 294:534-536, 2001.

Pende, D. et al., "Role of NKG2D in tumor cell lysis mediated by human NK cells: cooperation with natural cytotoxicity receptors and capability of recognizing tumors of nonepithelial origin," *Eur J Immunol*, 31(4):1076-1086, 2001.

Poggi, A. et al., "Vδ1 T lymphocytes from B-CLL patients recognize ULPB3 expressed on leukemic B cells and up-regulated by *trans*-retinoic acid," *Cancer Res*, 64:9172-9179, 2004.

Radaev, S. et al., "Conformational plasticity revealed by the cocrystal structure of NKG2D and its class I MHC-like ligand ULBP3," *Immunity* 15:1039-104, 2001.

Radosavljevic, M., et al., "A cluster of ten novel MHC class I related genes on human chromosome 6q24.2-q25.3," *Genomics* 79(1):114-123, 2002.

Rölle et al., "Effects of human cytomegalovirus infection on ligands for the activating of NKG2D receptor of NK cells: up-regulation of UL16-binding protein (ULBP)1 and ULBP2 is counteracted by the viral UL16 protein," *J. Immunol*. 171:902-908, 2003.

Ruehlmann, J.M. et al., "*MIG*(CXCL9) chemokine gene therapy combines with antibody-cytokine fusion protein to suppress growth and dissemination of murine colon carcinoma," *Cancer Res*, 61:8498-8503, 2001.

Scott et al., "The *pendred syndrome*gene encodes a chloride-iodide transport protein," *Nat Gen* 21:440-443, 1999.

Scott-Algara, D. and Paul P., "NK cells and HIV infection: Lessons from other viruses," *Curr Mol Med* 2:757-768, 2002.

Smith, C. et al., "CD30 antigen, a marker for Hodgkin's lymphoma, is a receptor whose ligand defines an emerging family of cytokines with homology to TNF," *Cell* 73:1349-1360, 1993.

Song et al., "Soluble ULBP suppresses natural killer cell activity via down-regulating NKG2D expression," *Cell. Inununol*. 239:22-30, 2006.

Spaggiari, G.M. et al., "Mesenchymal stem cell-natural killer cell interactions: evidence that activated NK cells are capable of killing MSCs, whereas MSCs can inhibit IL-2-induced NK-cell proliferation," *Blood*, 107(4):1484-1490, 2006.

Spies, T., "Regulation of NKG2D ligands: a purposeful but delicate affair," *Nat Immunol*, 9(9):1013-1015, 2008.

Steinle, A. et al., "Interactions of human NKG2D with its ligands MICA, MICB, and homologs of the mouse RAE-1 protein family," *Immunogenetics* 53:279-287, 2001.

Sun, T. et al., "Histiocyte-rich B-cell lymphoma," *Human Pathology* 28(11):1321-1324, 1997.

Sutherland, C.L. et al., "The UL16-binding proteins, a novel family of MHC class I-related ligands for NKG2D, activate natural killer cell functions," *Immunol Rev* 181:185-192, 2001.

Tieng, V. et al., "Binding of *Escherichia coli* adhesion AfaE to CD55 triggers cell-surface expression of the MHC class I-related molecule MICA," *Proc Natl Acad Sci*, 99(5):2977-2982, 2002.

Ugolini, S. and Vivier, E., "Multifaceted roles of MHC class I and MHC class I-like molecules in T cell activation," *Nature Immunol* 2(3):198-200, 2001.

Whiteside, T. and Herberman, R., "The role of natural killer cells in immune surveillance of cancer," *Curr Opth Immunol* 7:704-710, 1995.

Wiemann, K. et al., "Systemic NKG2D down-regulation impairs NK and CD8 T cell responses in vivo," *J lmmunol*, 175:720-729, 2005.

Wolan, D.W. et al., Crystal structure of the murine NK cell-activating receptor NKG2D at 1.95 Å, *Nat Immunol*, 2(3):248-254, 2001.

Wu, J. et al., "T cell antigen receptor engagement and specificity in the recognition of stress-inducible MHC class I-related chains by human epithelial γδ T cells," *J Immunol*, 169:1236-1240, 2002.

Yamabe et al., "Induction of the 2B9 antigen/dipeptidyl peptidase IV/CD26 on human natural killer cells by IL-2, IL-12 and IL-15," *Immunology* 91:151-158, 1997.

Zamai, L. et al. "NK Cells and Cancer", *J Immunol*, 178:4011-4016, 2007.

GenBank Accession No. AAD12613 (2001).
A_Geneseq_21 Accession No. AAG68335 (2002).
GenBank Accession No. AAY36021 (1999).
GenBank Accession No. AI091180 (1997).
GenBank Accession No. AL602601 (2001).
GenBank Accession No. AX191626 (2001).
GenBank Accession No. BI258059 (2001).
GenBank Accession No. R25716 (1995).
GenBank Accession No. AAX97755 (1999).
NCBI Accession No. AAL11005 (2001).
NCBI Accession No. AAL76417 (2001).
NCBI Accession No. AL355312 (2001).
NCBI Accession No. AF359243 (2001).
NCBI Accession No. AY054974 (2001).
NCBI Accession No. AY069961 (2002).
NCBI Accession No. BE545401 (2000).
NCBI Accession No. NM_139165 (2002).
NCBI Accession No. XM_059764 (2002).
NCBI Accession No. AAL58090 (2004).

\* cited by examiner

Percent cytotoxicity

SEQUENCE LISTING

<160> NUMBER OF SEQ ID NOS: 11

<210> SEQ ID NO 1
<211> LENGTH: 792
<212> TYPE: DNA
<213> ORGANISM: Homo sapiens

<400> SEQUENCE: 1

```
atgcgaagaa tatccctgac ttctagccct gtgcgccttc ttttgtttct gctgttgcta      60
ctaatagcct tggagatcat ggttggtggt cactctcttt gcttcaactt cactataaaa     120
tcattgtcca gacctggaca gccctggtgt gaagcgcagg tcttcttgaa taaaaatctt     180
ttccttcagt acaacagtga caacaacatg gtcaaacctc tgggcctcct ggggaagaag     240
gtatatgcca ccagcacttg gggagaattg acccaaacgc tgggagaagt ggggcgagac     300
ctcaggatgc tcctttgtga catcaaaccc cagataaaga ccagtgatcc ttccactctg     360
caagtcgaga tgttttgtca acgcgaagca gaacggtgca ctggtgcatc ctggcagttc     420
gccaccaatg gagagaaatc cctcctcttt gacgcaatga acatgacctg gacagtaatt     480
aatcatgaag ccagtaagat caaggagaca tggaagaaag acagagggct ggaaaagtat     540
ttcaggaagc tctcaaaggg agactgcgat cactggctca gggaattctt agggcactgg     600
gaggcaatgc cagaaccgac agtgtcacca gtaaatgctt cagatatcca ctggtcttct     660
tctagtctac cagatagatg gatcatcctg ggggcattca tcctgttagt tttaatggga     720
attgttctca tctgtgtctg gtggcaaaat ggtgagtggc aggctggtct ctggcccttg     780
aggacgtctt ag                                                         792
```

<210> SEQ ID NO 2
<211> LENGTH: 263
<212> TYPE: PRT
<213> ORGANISM: Homo sapiens

<400> SEQUENCE: 2

```
Met Arg Arg Ile Ser Leu Thr Ser Ser Pro Val Arg Leu Leu Leu Phe
1               5                   10                  15

Leu Leu Leu Leu Leu Ile Ala Leu Glu Ile Met Val Gly Gly His Ser
                20                  25                  30

Leu Cys Phe Asn Phe Thr Ile Lys Ser Leu Ser Arg Pro Gly Gln Pro
            35                  40                  45

Trp Cys Glu Ala Gln Val Phe Leu Asn Lys Asn Leu Phe Leu Gln Tyr
        50                  55                  60

Asn Ser Asp Asn Asn Met Val Lys Pro Leu Gly Leu Leu Gly Lys Lys
65                  70                  75                  80
```

```
Val Tyr Ala Thr Ser Thr Trp Gly Glu Leu Thr Gln Thr Leu Gly Glu
                85                  90                  95

Val Gly Arg Asp Leu Arg Met Leu Leu Cys Asp Ile Lys Pro Gln Ile
            100                 105                 110

Lys Thr Ser Asp Pro Ser Thr Leu Gln Val Glu Met Phe Cys Gln Arg
            115                 120                 125

Glu Ala Glu Arg Cys Thr Gly Ala Ser Trp Gln Phe Ala Thr Asn Gly
        130                 135                 140

Glu Lys Ser Leu Leu Phe Asp Ala Met Asn Met Thr Trp Thr Val Ile
145                 150                 155                 160

Asn His Glu Ala Ser Lys Ile Lys Glu Thr Trp Lys Lys Asp Arg Gly
                165                 170                 175

Leu Glu Lys Tyr Phe Arg Lys Leu Ser Lys Gly Asp Cys Asp His Trp
            180                 185                 190

Leu Arg Glu Phe Leu Gly His Trp Glu Ala Met Pro Glu Pro Thr Val
        195                 200                 205

Ser Pro Val Asn Ala Ser Asp Ile His Trp Ser Ser Ser Leu Pro
    210                 215                 220

Asp Arg Trp Ile Ile Leu Gly Ala Phe Ile Leu Val Leu Met Gly
225                 230                 235                 240

Ile Val Leu Ile Cys Val Trp Gln Asn Gly Glu Trp Gln Ala Gly
                245                 250                 255

Leu Trp Pro Leu Arg Thr Ser
            260

<210> SEQ ID NO 3
<211> LENGTH: 244
<212> TYPE: PRT
<213> ORGANISM: Homo sapiens

<400> SEQUENCE: 3

Met Ala Ala Ala Ser Pro Ala Phe Leu Leu Cys Leu Pro Leu Leu
1               5                   10                  15

His Leu Leu Ser Gly Trp Ser Arg Ala Gly Trp Val Asp Thr His Cys
                20                  25                  30

Leu Cys Tyr Asp Phe Ile Ile Thr Pro Lys Ser Arg Pro Glu Pro Gln
            35                  40                  45

Trp Cys Glu Val Gln Gly Leu Val Asp Glu Arg Pro Phe Leu His Tyr
        50                  55                  60

Asp Cys Val Asn His Lys Ala Lys Ala Phe Ala Ser Leu Gly Lys Lys
65                  70                  75                  80

Val Asn Val Thr Lys Thr Trp Glu Glu Gln Thr Glu Thr Leu Arg Asp
                85                  90                  95

Val Val Asp Phe Leu Lys Gly Gln Leu Leu Asp Ile Gln Val Glu Asn
            100                 105                 110

Leu Ile Pro Ile Glu Pro Leu Thr Leu Gln Ala Arg Met Ser Cys Glu
            115                 120                 125

His Glu Ala His Gly His Gly Arg Gly Ser Trp Gln Phe Leu Phe Asn
        130                 135                 140

Gly Gln Lys Phe Leu Leu Phe Asp Ser Asn Asn Arg Lys Trp Thr Ala
145                 150                 155                 160

Leu His Pro Gly Ala Lys Lys Met Thr Glu Lys Trp Glu Lys Asn Arg
                165                 170                 175

Asp Val Thr Met Phe Phe Gln Lys Ile Ser Leu Gly Asp Cys Lys Met
            180                 185                 190
```

```
Trp Leu Glu Glu Phe Leu Met Tyr Trp Gln Met Leu Asp Pro Thr
            195                 200                 205
Lys Pro Pro Ser Leu Ala Pro Gly Thr Thr Gln Pro Lys Ala Met Ala
210                 215                 220
Thr Thr Leu Ser Pro Trp Ser Leu Leu Ile Ile Phe Leu Cys Phe Ile
225                 230                 235                 240
Leu Ala Gly Arg

<210> SEQ ID NO 4
<211> LENGTH: 246
<212> TYPE: PRT
<213> ORGANISM: Homo sapiens

<400> SEQUENCE: 4

Met Ala Ala Ala Ala Thr Lys Ile Leu Leu Cys Leu Pro Leu Leu
1               5                   10                  15
Leu Leu Leu Ser Gly Trp Ser Arg Ala Gly Arg Ala Asp Pro His Ser
            20                  25                  30
Leu Cys Tyr Asp Ile Thr Val Ile Pro Lys Phe Arg Pro Gly Pro Arg
        35                  40                  45
Trp Cys Ala Val Gln Gly Gln Val Asp Glu Lys Thr Phe Leu His Tyr
50                  55                  60
Asp Cys Gly Asn Lys Thr Val Thr Pro Val Ser Pro Leu Gly Lys Lys
65                  70                  75                  80
Leu Asn Val Thr Thr Ala Trp Lys Ala Gln Asn Pro Val Leu Arg Glu
                85                  90                  95
Val Val Asp Ile Leu Thr Glu Gln Leu Arg Asp Ile Gln Leu Glu Asn
            100                 105                 110
Tyr Thr Pro Lys Glu Pro Leu Thr Leu Gln Ala Arg Met Ser Cys Glu
        115                 120                 125
Gln Lys Ala Glu Gly His Ser Ser Gly Ser Trp Gln Phe Ser Phe Asp
    130                 135                 140
Gly Gln Ile Phe Leu Leu Phe Asp Ser Glu Lys Arg Met Trp Thr Thr
145                 150                 155                 160
Val His Pro Gly Ala Arg Lys Met Lys Glu Lys Trp Glu Asn Asp Lys
                165                 170                 175
Val Val Ala Met Ser Phe His Tyr Phe Ser Met Gly Asp Cys Ile Gly
            180                 185                 190
Trp Leu Glu Asp Phe Leu Met Gly Met Asp Ser Thr Leu Glu Pro Ser
        195                 200                 205
Ala Gly Ala Pro Leu Ala Met Ser Ser Gly Thr Thr Gln Leu Arg Ala
    210                 215                 220
Thr Ala Thr Thr Leu Ile Leu Cys Cys Leu Leu Ile Ile Leu Pro Cys
225                 230                 235                 240
Phe Ile Leu Pro Gly Ile
                245

<210> SEQ ID NO 5
<211> LENGTH: 244
<212> TYPE: PRT
<213> ORGANISM: Homo sapiens

<400> SEQUENCE: 5

Met Ala Ala Ala Ala Ser Pro Ala Ile Leu Pro Arg Leu Ala Ile Leu
1               5                   10                  15
Pro Tyr Leu Leu Phe Asp Trp Ser Gly Thr Gly Arg Ala Asp Ala His
```

```
                20                  25                  30
Ser Leu Trp Tyr Asn Phe Thr Ile Ile His Leu Pro Arg His Gly Gln
        35                  40                  45

Gln Trp Cys Glu Val Gln Ser Gln Val Asp Gln Lys Asn Phe Leu Ser
 50                  55                  60

Tyr Asp Cys Gly Ser Asp Lys Val Leu Ser Met Gly His Leu Glu Glu
 65                  70                  75                  80

Gln Leu Tyr Ala Thr Asp Ala Trp Gly Lys Leu Glu Met Leu Arg
                85                  90                  95

Glu Val Gly Gln Arg Leu Arg Leu Glu Leu Ala Asp Thr Glu Leu Glu
                100                 105                 110

Asp Phe Thr Pro Ser Gly Pro Leu Thr Leu Gln Val Arg Met Ser Cys
        115                 120                 125

Glu Cys Glu Ala Asp Gly Tyr Ile Arg Gly Ser Trp Gln Phe Ser Phe
        130                 135                 140

Asp Gly Arg Lys Phe Leu Leu Phe Asp Ser Asn Asn Arg Lys Trp Thr
145                 150                 155                 160

Val Val His Ala Gly Ala Arg Arg Met Lys Glu Lys Trp Glu Lys Asp
                165                 170                 175

Ser Gly Leu Thr Thr Phe Phe Lys Met Val Ser Met Arg Asp Cys Lys
                180                 185                 190

Ser Trp Leu Arg Asp Phe Leu Met His Arg Lys Arg Leu Glu Pro
                195                 200                 205

Thr Ala Pro Pro Thr Met Ala Pro Gly Leu Ala Gln Pro Lys Ala Ile
        210                 215                 220

Ala Thr Thr Leu Ser Pro Trp Ser Phe Leu Ile Ile Leu Cys Phe Ile
225                 230                 235                 240

Leu Pro Gly Ile

<210> SEQ ID NO 6
<211> LENGTH: 257
<212> TYPE: PRT
<213> ORGANISM: Homo sapiens
<220> FEATURE:
<221> NAME/KEY: MISC_FEATURE
<222> LOCATION: (16)..(16)
<223> OTHER INFORMATION: "Xaa is unknown"
<220> FEATURE:
<221> NAME/KEY: MISC_FEATURE
<222> LOCATION: (123)..(124)
<223> OTHER INFORMATION: "Xaa is unknown"
<220> FEATURE:
<221> NAME/KEY: MISC_FEATURE
<222> LOCATION: (166)..(166)
<223> OTHER INFORMATION: "Xaa is unknown"
<220> FEATURE:
<221> NAME/KEY: MISC_FEATURE
<222> LOCATION: (176)..(176)
<223> OTHER INFORMATION: "Xaa is unknown"
<220> FEATURE:
<221> NAME/KEY: MISC_FEATURE
<222> LOCATION: (179)..(179)
<223> OTHER INFORMATION: "Xaa is unknown"
<220> FEATURE:
<221> NAME/KEY: MISC_FEATURE
<222> LOCATION: (205)..(205)
<223> OTHER INFORMATION: "Xaa is unknown"
<220> FEATURE:
<221> NAME/KEY: MISC_FEATURE
<222> LOCATION: (207)..(207)
<223> OTHER INFORMATION: "Xaa is unknown"
<220> FEATURE:
<221> NAME/KEY: MISC_FEATURE
<222> LOCATION: (211)..(211)
<223> OTHER INFORMATION: "Xaa is unknown"
```

```
<220> FEATURE:
<221> NAME/KEY: MISC_FEATURE
<222> LOCATION: (215)..(215)
<223> OTHER INFORMATION: "Xaa is unknown"
<220> FEATURE:
<221> NAME/KEY: MISC_FEATURE
<222> LOCATION: (222)..(222)
<223> OTHER INFORMATION: "Xaa is unknown"
<220> FEATURE:
<221> NAME/KEY: MISC_FEATURE
<222> LOCATION: (225)..(226)
<223> OTHER INFORMATION: "Xaa is unknown"
<220> FEATURE:
<221> NAME/KEY: MISC_FEATURE
<222> LOCATION: (237)..(237)
<223> OTHER INFORMATION: "Xaa is unknown"
<220> FEATURE:
<221> NAME/KEY: MISC_FEATURE
<222> LOCATION: (252)..(253)
<223> OTHER INFORMATION: "Xaa is unknown"
<220> FEATURE:
<221> NAME/KEY: MISC_FEATURE
<222> LOCATION: (256)..(257)
<223> OTHER INFORMATION: "Xaa is unknown"

<400> SEQUENCE: 6
```

Met Arg Arg Ile Ser Leu Thr Ser Ser Pro Val Arg Leu Leu Leu Xaa
1               5                   10                  15

Leu Leu Leu Leu Leu Ile Ala Leu Glu Ile Met Val Gly Gly His Ser
            20                  25                  30

Leu Cys Phe Asn Phe Thr Ile Lys Ser Leu Ser Arg Pro Gly Gln Pro
        35                  40                  45

Trp Cys Glu Ala His Val Phe Leu Asn Lys Asn Leu Phe Leu Gln Tyr
    50                  55                  60

Asn Ser Asp Asn Met Val Lys Pro Leu Gly Leu Leu Gly Lys Lys
65                  70                  75                  80

Val Tyr Ala Thr Ser Thr Trp Gly Glu Leu Thr Gln Thr Leu Gly Glu
            85                  90                  95

Val Gly Arg Asp Leu Arg Met Leu Leu Cys Asp Ile Lys Pro Gln Ile
            100                 105                 110

Lys Thr Ser Asp Pro Ser Thr Leu Gln Val Xaa Xaa Phe Cys Gln Arg
            115                 120                 125

Glu Ala Glu Arg Cys Thr Gly Ala Ser Trp Gln Phe Ala Thr Asn Gly
            130                 135                 140

Glu Lys Ser Leu Leu Phe Asp Ala Met Asn Met Thr Trp Thr Val Ile
145                 150                 155                 160

Asn His Glu Ala Ser Xaa Ile Lys Glu Thr Trp Lys Lys Asp Arg Xaa
                165                 170                 175

Leu Glu Xaa Tyr Phe Arg Lys Leu Ser Lys Gly Asp Cys Asp His Trp
            180                 185                 190

Leu Arg Glu Phe Leu Gly His Trp Glu Ala Met Pro Xaa Pro Xaa Val
            195                 200                 205

Ser Pro Xaa Asn Ala Ser Xaa Ile His Trp Ser Ser Ser Xaa Leu Pro
            210                 215                 220

Xaa Xaa Trp Ile Ile Leu Gly Ala Phe Ile Leu Leu Xaa Leu Met Gly
225                 230                 235                 240

Ile Val Leu Ile Cys Val Trp Trp Gln Asn Gly Xaa Xaa Ser Thr Xaa
            245                 250                 255

Xaa

```
<210> SEQ ID NO 7
<211> LENGTH: 36
```

```
<212> TYPE: DNA
<213> ORGANISM: Artificial Sequence
<220> FEATURE:
<223> OTHER INFORMATION: primer

<400> SEQUENCE: 7
tatgtcgacc tccacagtat gcgaagaata tccctg                             36

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
ataggcggcc gcagactaag acgtcctcaa                                    30

<210> SEQ ID NO 9
<211> LENGTH: 39
<212> TYPE: DNA
<213> ORGANISM: Artificial Sequence
<220> FEATURE:
<223> OTHER INFORMATION: probe

<400> SEQUENCE: 9
gagtggcagg ctggtctctg gcccttgagg acgtcttag                          39

<210> SEQ ID NO 10
<211> LENGTH: 20
<212> TYPE: PRT
<213> ORGANISM: HOMO SAPIENS

<400> SEQUENCE: 10

Met Glu Thr Asp Thr Leu Leu Leu Trp Val Leu Leu Leu Trp Val Pro
1               5                   10                  15
Gly Ser Thr Gly
            20

<210> SEQ ID NO 11
<211> LENGTH: 26
<212> TYPE: PRT
<213> ORGANISM: HOMO SAPIENS

<400> SEQUENCE: 11

Met Ala Thr Gly Ser Arg Thr Ser Leu Leu Leu Ala Phe Gly Leu Leu
1               5                   10                  15
Cys Leu Pro Trp Leu Gln Glu Gly Ser Ala
            20                  25
```

UL16 BINDING PROTEIN 4

CROSS REFERENCE TO RELATED APPLICATIONS

This application a divisional of U.S. patent application Ser. No. 10/265,811, filed Oct. 4, 2002, now U.S. Pat. No. 7,563,450, issued Jul. 21, 2009, which claims the benefit of U.S. provisional application No. 60/327,252, filed Oct. 4, 2001.

REFERENCE TO THE SEQUENCE LISTING

The present application is being filed along with a Sequence Listing in electronic format. The Sequence Listing is provided as a file entitled 3205-US-DIV_Seq_Listing.txt, created May 16, 2006, which is 15 KB in size. The information in the electronic format of the Sequence listing is incorporated herein by reference in its entirety.

FIELD OF THE INVENTION

The invention generally relates to a novel member of the UL6 binding protein (ULBP) family, ULBP4. More specifically, the invention relates to purified and isolated ULBP4 polypeptides, nucleic acid molecules encoding the polypeptides, and processes for production and use of ULBP polypeptides.

BACKGROUND

The ULBPs (UL16 binding proteins) are a novel family of human, MHC class 1-related cell-surface proteins. ULBP1 was identified as a polypeptide that bound to the human cytomegalovirus (HCMV)glycoprotein, UL16 (Cosman et al., 2001, Immunity 14:123-133). ULBP2 and ULBP3 were subsequently discovered and have some homology to ULBP1 (Id.). ULBP polypeptides share some, but not all of the features of MHC Class 1 proteins. The ULBPs have alpha-1 and alpha-2 domains characteristic of MHC class 1 proteins, but lack an alpha-3 domain and do not associate with beta-2 microglobulin. Id.

Some members of another family of human nonclassical MHC Class 1 proteins, the MICs, also bind UL16. Groh et al. (1996) PNAS USA 93: 12445. MICA and MICB polypeptides share some similar properties with the ULBPs, as discussed below.

The ULBPs and MICs are important activators of natural killer (NK) cells, which are a key component of the innate immune system. Activated NK cells recognize and lyse targeted cells, such as virus-infected and neoplastic cells.

NK cells recognize signals from cellular targets via receptors that are specific for MHC class 1 molecules on the target cell. These NK cell receptors include the killer cell Ig-like receptor (KIR), Ly49, and NKG2 receptor families. Depending on the structure of the receptor, engagement with a specific ligand will deliver either activating or inhibitory signals to the NK cell. Lanier (1998). Ann Rev Immunol 16: 359. Until recently, it was thought that signals generated by inhibitory NK cell receptors (KIRs) were dominant over those generated by any activating receptor, so that cells with down-regulated MHC class 1 levels would be killed, according to the "missing-self" hypothesis. Ljunggren et al. (11990). Immunology Today 11: 237. However, expression of the activating ligands, ULBPs or MICs, on NK cell-resistant, MHC class 1-expressing target cells renders the cells susceptible to NK cell killing. Cosman et al., supra; Bauer et al. (1999). Science 285:727-29. In addition, soluble, recombinant forms of the ULBPs, when administered to human NK cells, have now been found to bind to the NK cells and stimulate NK cytotoxicity against tumor targets. Kubin et al. (2001), Eur. J. Immunol. 31: 1428-37. ULBPs and MICs transduce an activating signal to NK cells that can override a negative signal generated by engagement of inhibitory receptors for MHC class 1 antigens.

ULBPs have been found to induce NK cell production of the cytokines IFN-gamma. GM-CSF, TNF-alpha, and TNF-beta, and the chemokines MIP1-alpha. MIP1-beta, and 1-309. Co-stimulation of NK cells with IL-12 has a superadditive effect on production of these factors. Cosman et al. supra: Kubin et al., supra.

MICA expression is upregulated in certain epithelial tumors, in HCMV-infected cells, and in response to stress. Groh et al. (1996), PNAS USA 93: 12445-50; Groh et al. (1999). PNAS USA 96: 6879-84. In contrast to the MICs, ULBP messages are expressed by a wide range of cells, tissues, and tumors, and on various cell lines (Cosman et al., supra). Thus, several types of cells may potentially deliver ULBP-mediated signals to NK cells and be targets of ULBP-mediated killing.

Although the amino acid sequences of the ULBPs and MICs are only distantly related, both families of proteins deliver an activating signal to NK cells by binding to NKG2D/DAP10 heterocomplexes. NKG2D is a homodimeric, C-type lectin that is expressed not only on human NK cells, but also on human CD8$^+$ $\alpha\beta$ T cells and $\gamma\delta$ T cells. NKG2D expression has also been reported on mrine NK cells and on activated murine CD8$^+$ $\alpha\beta$ T cells and macrophages. Bauer, supra; Diefenbach et al. (2000). Nature Immunol. 1: 119-126). In T cells, NKG2D acts as a costimulatory receptor, in a similar manner as CD28. Groh et al. (2001), Nature Immunol. 2: 255. The cytoplasmic domain of NKG2D is short, and signaling is mediated through its association with the DAP10 membrane adapter protein. Wu et al. (1999), Science 285:730-32. DAP10 can bind the p85 subunit of PI 3-kinase and the adapter protein Grb2. Wu et al., supra; Chang et al. (1999), J. Immunol. 163: 4651-54.

ULBP1, 2, and 3 polypeptides bind to recombinantly expressed NKG2D/DAP10 heterodimers. Anti-NKG2D antibodies block binding of ULBP 1, 2, and 3 to NK cells. Cosman et al., supra; Sutherland et al. (2002), J. Immunol. 168 (2): 671-79. This evidence supports a conclusion that NKG2D is the receptor expressed on primary human NK cells that recognizes ULBP.

Agents that are effective to activate NK cell, T cell, or macrophage activity, to induce cellular production of chemokines and cytokines, and to induce target cell cytotoxicity are useful for target cell lysis, particularly for lysis of pathogen-infected cells and tumor cells. New ligands having the ability to activate NK cells. T cells, macrophages, particularly via the NKG2D/DAP10 receptor complex, are useful as agents for activating therapeutic responses from immune effector cells, for example by eliciting NK cell and/or T cell killing and other NK cell and/or T cell dependent therapies. NKG2D/DAP10 receptors are expressed on $\gamma\delta$ T cells, CD8$^+$ T cells, and macrophages. Bauer et al (1999), Science 285: 727-29; Diefenbach et al. (2000), Nature Immunology 1(2): 119-26. Engagement of these receptors can stimulate T cell proliferation, cytotoxicity, and cytokine production. Groh et al. (2001), Nature Immunol. 2:255: Das et al. (2001), Immunity 15:83-93.

SUMMARY OF THE INVENTION

The present invention provides ULBP4, a novel member of the ULBP family of proteins. ULBP4 polypeptides of the invention include those having an amino acid sequence shown in SEQ ID NO:2, as well as polypeptides having substantial amino acid sequence identity to the amino acid sequence of SEQ ID NO:2 and useful fragments thereof. Useful fragments include those that can bind to NKG2D. Such ULBP4 polypeptides can have the capacity to activate immune effector cells, including NK cells and T cells, expressing NKG2D.

The invention also provides a polynucleotide molecule encoding ULBP4 polypeptides. Polynucleotide molecules of the invention include the following: those molecules having a nucleic acid sequence as shown in SEQ ID NO:1; those that hybridize to the nucleic acid sequence of SEQ ID NO:1 under high stringency hybridization conditions (for example, 42° C., 6×SSC, 50% formamide); those that encode a ULBP4 protein having substantial sequence identity to SEQ ID NO:2; and those having substantial nucleic acid sequence identity with the nucleic acid sequence of SEQ ID NO:1.

The invention includes variants and derivatives of the ULBP4 polypeptide, including soluble forms and fusion proteins. Soluble forms of ULBP proteins are soluble in aqueous solutions and can, for example, include an extracellular domain and lack a transmembrane region or a GPI anchor. Fusion proteins of the invention include a ULBP4 polypeptide fused to a heterologous protein or peptide that confers a desired function. The heterologous protein or peptide can facilitate purification, oligomerization, stability, secretion, or targeting of the ULBP4 polypeptide, for example. The fusion proteins of the invention can be produced, for example, from an expression construct containing a polynucleotide molecule encoding ULBP4 polypeptide in frame with a polynucleotide molecule encoding the heterologous protein. The invention also provides vectors, plasmids, expression systems, host cells, and the like, containing the ULBP4 polynucleotide molecule of the invention. Genetic engineering methods for the production of ULBP4 polypeptides of the invention include expression of the polynucleotide molecules in cell free expression systems, in cellular hosts, in tissues, and in animal models, according to known methods.

The invention further includes pharmaceutical compositions containing a substantially purified ULBP polypeptide of the invention and a pharmaceutically acceptable carrier. Such pharmaceutical compositions are administered to cells, tissues, or patients, for example, to induce the activity of NKG2D/DAP10-expressing cells, including NK cells, T cells, and activated macrophages; to induce the production of cytokines and chemokines; to induce lysis of tumor cells and infected cells such as virally infected cells by enhancing the cytotoxicity of NKG2D/DAP10-expressing cells; and for therapeutic treatment, for example, of cancer, viral infections, and bacterial infections.

Anti-ULBP4 antibodies are also provided. Anti-ULBP antibodies, including those that bind to ULBP1, ULBP2, UBLP3, and/or ULBP4, can be used, for example, to target therapeutic agents to ULBP-expressing cells, to induce antibody-dependent cell-mediated cytotoxicity against ULBP-expressing cells, to downmodulate an immune response, and/or to purify, identify, or assure the quality of a ULBP protein. Such antibodies can have a variety of properties: they can bind to ULBP polypeptides; they may be human or humanized; they may be antagonistic, that is, they may prevent or inhibit the activation of NKG2D-expressing cells by the interaction of a ULBP protein and NKG2D; they may or may not inhibit the binding of ULBP protein to NKG2D; and/or they may be fused to a cytotoxic or radioactive agent.

The invention also provides reagents, compositions, and methods that are useful for analysis of NKG2D-expressing cell activity; for analysis of NKG2D receptor engagement and activation; and for analysis of the inhibitory/stimulatory effects of signal molecules involved in the innate immune system response to infection and to neoplastic cells.

Therapeutic methods of the invention include the use of ULBP polypeptides and/or anti-ULBP antibodies in numerous applications including: the treatment of tumors, in which the tumor cells may or may not express ULBP proteins; the treatment of infections including viral and/or bacterial infections; the down modulation of an immune response in patients experiencing, for example, an autoimmune disease, a transplant, or an inflammatory bowel disease, among many possible applications.

The invention further provides a method for vaccinating a patient against tumor regrowth which includes: surgically removing a tumor; culturing tumor cells from the removed tumor; transfecting the cultured tumor cells with a nucleic acid encoding the ULBP4 protein of claim 1; irradiating the cultured tumor cells; and reintroducing the irradiated, transfected tumor cells into the patient.

These and various other features and advantages of the invention will be apparent from a reading of the following detailed description and a review of the appended claims.

BRIEF DESCRIPTION OF THE SEQUENCES

Figure 1:
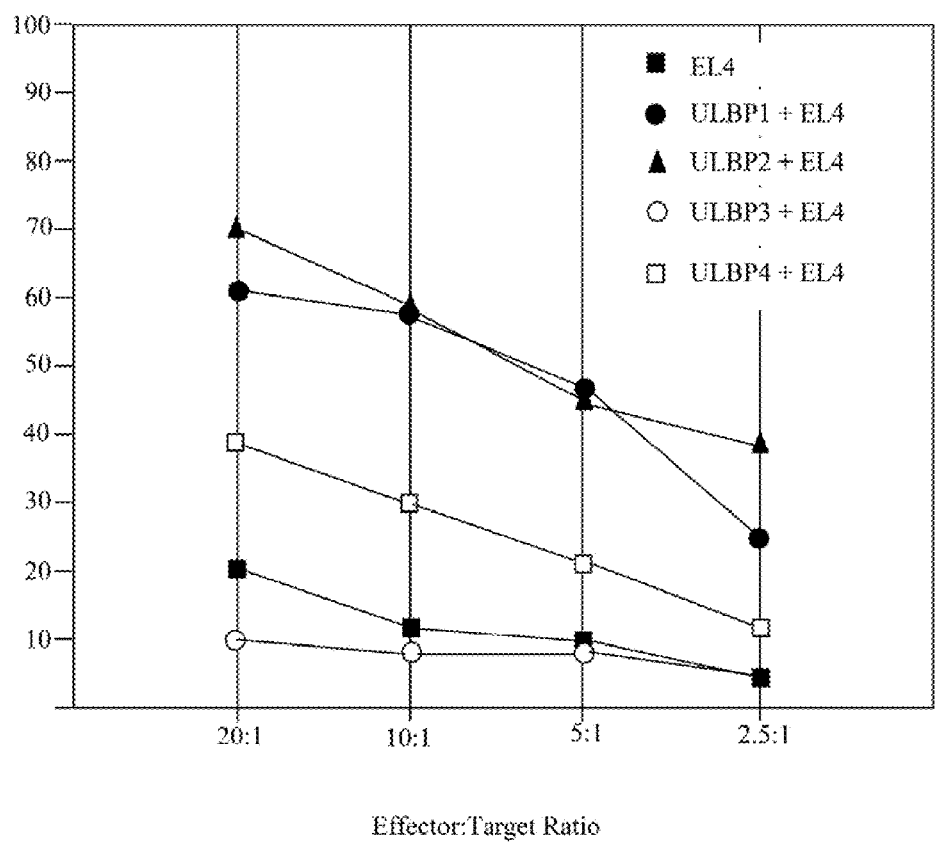
FIG. 1 shows the percent cytotoxicity of murine NK cells (effector cells) when combined with target cells, either $^{51}$Cr-labeled untransfected EL4 cells or $^{51}$Cr-labeled EL4 cells that have been transfected with nucleic acids encoding the indicated ULBP protein, as a function of the effector cell:target cell ratio.

SEQ ID NO:1 is a nucleic acid sequence encoding ULBP4.
SEQ ID NO:2 is the amino acid sequence encoded by SEQ ID NO:1.
SEQ ID NO:3 is an amino acid sequence of ULBP1.
SEQ ID NO:4 is an amino acid sequence of ULBP2.
SEQ ID NO:5 is an amino acid sequence of ULBP3.
SEQ ID NO:6 is an amino acid sequence predicted for a cDNA disclosed in WO 9931236.
SEQ ID NO:7 is a nucleic acid primer.
SEQ ID NO:8 is a nucleic acid primer.
SEQ ID NO:9 is a 3' segment of SEQ ID NO:1.
SEQ ID NO: 10 is the signal sequence of human IgK.
SEQ ID NO:11 is the signal sequence of human growth hormone.

DETAILED DESCRIPTION OF THE INVENTION

Definitions

The following definitions are provided to facilitate understanding of certain terms used frequently herein and are not meant to limit the scope of the present disclosure.

"Activating" an immune effector cell, such as an NK cell or a T cell, means stimulating the cell to engage in an inflammatory response that can include, for example, lysis of target cells (or enhancement of the cytotoxicity of the of the immune effector cell) and/or secretion of inflammatory cytokines and/or chemokines. Immune effector cells may be activated "in vitro" (that is, while in cell culture). "in vivo" (that is, while the cells are part of a living mammal), and/or "ex vivo" (that is, activated while in culture but later returned to a living mammal).

"Akt" refers to a serine/threonine protein kinase involved in anti-apoptotic signaling within cells. Blume-Jensen et al. (2001), Nature 411(6835): 355-365. Illustrative techniques for determining serine/threonine protein kinase activity are shown in *Current Protocols in Molecular Biology*, Ausubel et al. eds. (Wiley & Sons, New York, (1988) and quarterly updates). Activation of Akt can be assayed by immunoblotting for the activated, phosphorylated form of the protein. An antibody to Akt (Ser473) is available from Cell Signaling Technology (Beverly, Mass.). In addition, a kit for assessing activation of Akt is available from Upstate Biotechnology (Lake Placid. NY).

"Amino acid" refers to any of the twenty naturally occurring amino acids as well as any modified amino acid sequences. Modifications may include natural processes such as posttranslational processing, or may include chemical modifications which are known in the art. Modifications include but are not limited to: phosphorylation, ubiquitination, acetylation, amidation, glycosylation, covalent attachment of flavin, ADP-ribosylation, cross-linking, iodination, methylation, and the like.

"Antibody" is used herein in its broadest sense, and specifically includes native and genetically engineered, monoclonal and polyclonal, single and double chain, chimeric, humanized, bispecific, diabodies, and fragments of these that retain antigen binding activity. Fragments include Fab, Fc, and Fv.

"Antisense" refers to polynucleotide sequences that are complementary to target "sense" polynucleotide sequence.

"Cell targeting moiety" refers to any signal on a polypeptide, either naturally occurring or genetically engineered, used to target the polypeptide to a cell. Targeting moieties include ligands that bind to a cellular antigen or receptor, such as antibodies and receptor ligands. Specific examples of ligand/receptor pairs include epidermal growth factor (EGF) and the EGF receptor, anti-PS1 antibody and the PS1 antigen present on prostate cancer cells, and the like. Many such cell-specific ligand/receptor pairs are known and are useful in the present invention, for example, in fusion proteins to deliver ULBP polypeptides to a target cell.

"Complementary" or "complementarity" refers to the ability of a polynucleotide in a polynucleotide molecule to form a base pair with another polynucleotide in a second polynucleotide molecule. For example, the sequence A-G-T is complementary to the sequence T-C-A. Complementarity may be partial, in which only some of the polynucleotides match according to base pairing, or complete, where all the polynucleotides match according to base pairing.

"Expression" refers to transcription and, optionally, translation occurring within a host cell. The level of expression of a polynucleotide molecule in a host cell tray be determined on the basis of either the amount of corresponding mRNA that is present within the cell or the amount of DNA molecule-encoded protein produced by the host cell (Sambrook et al., 1989, *Molecular Cloning: A Laboratory Manual*, 18.1-18.88).

"Fc" or "Fc polypeptide" refers to both native and mutant forms of the Fc region of an antibody that contain one or more of the Fc region's $C_H$ domains, including truncated forms of Fc polypeptides containing the dimerization-promoting hinge region. For example, Fc polypeptides derived from human IgG antibodies, including but not limited to IgG1, IgG2, and IgG3 antibodies can be used in the fusion proteins of the invention. One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., ((1994), EMBO J. 13: 3992-4001). The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

"Fusion protein" refers to a first protein linked to a second, heterologous protein. Preferably, the heterologous protein is fused via genetic engineering techniques, such that the first and second proteins are expressed in frame. The heterologous protein can confer a desired characteristic to the fusion protein, for example, a detection signal, enhanced stability or stabilization of the protein in a cell, facilitated oligomerization of the protein, facilitated purification of the fusion protein, targeting to a desired cell or tissue, or an additional biological activity such as, for example, activation of immune effector cells. Examples of heterologous proteins useful in the fusion proteins of the invention include immunoglobulin molecules and portions thereof, peptide tags such as histidine tag (6-His), leucine zipper, cytokines, growth factors, cell targeting moieties, signal peptides, therapeutic agents, and the like.

"Genetically engineered" refers to any recombinant DNA or RNA method used to create a eukaryotic host cell that expresses a target protein at elevated levels, at lowered levels, or in a mutated form. In other words, a recombinant polynucleotide molecule has been introduced into the host cell, thereby altering the cells so as to alter expression of the desired protein. Methods and vectors for genetically engineering host cells are well known in the art; for example various techniques are illustrated in *Current Protocols in Molecular Biology*, Ausubel et al., eds. (Wiley & Sons, New York, 1988, and quarterly updates). Genetical engineering techniques include but are not limited to expression vectors, targeted homologous recombination and gene activation (see, for example, U.S. Pat. No. 5,272,071 to Chappel) and trans activation by engineered transcription factors (see, for example, Segal et al. 1999, *Proc Natl Acad Sci USA* 96(6): 2758-63).

"Homology" refers to a degree of complementarity between polynucleotides, having significant effect on the efficiency and strength of hybridization between polynucleotide molecules.

"Host cell" or "host cells" refers to cells expressing a heterologous polynucleotide molecule. Host cells of the present invention express polynucleotides encoding ULBP4 or express a receptor enabling the cells to respond to ULBP4. Examples of suitable host cells useful in the present invention include, but are not limited to, insect and mammalian cells. Specific examples of such cells include SF9 insect cells (Summers and Smith, 1987, *Texas Agriculture Experiment Station Bulletin*, 1555), human embyonic kidney cells (293 cells), Chinese hamster ovary (CHO) cells (Puck et al., 1958,

*Proc. Natl. Acad. Sci. USA* 60:1275-1281), human cervical carcinoma cells (HELA) (ATCC CCL 2), human liver cells (Hep G2) (ATCC HB8065), human breast cancer cells (MCF-7) (ATCC HTB22), human colon carcinoma cells (DLD-1) (ATCC CCL 221), Daudi cells (ATCC CRL-213). CV-1 cells and the like.

"Hybridization" refers to the pairing of complementary polynucleotides during an annealing period. The strength of hybridization between two polynucleotide molecules is impacted by the homology between the two molecules, stringency of the conditions involved, the melting temperature of the formed hybrid and the G:C ratio within the polynucleotides.

The basic parameters affecting the choice of hybridization conditions and guidance for devising suitable conditions are set forth in Sambrook, J., E. F. Fritsch, and T. Maniatis ((1989), *Molecular Cloning: A Laboratory Manual*, Cold Spring Harbor Laboratory Press, Cold Spring Harbor, N.Y., chapters 9 and 11) and in *Current Protocols in Molecular Biology* (F. M. Ausubel et al., eds., John Wiley & Sons, Inc., sections 2.10 and 6.3-6.4). These parameters and suitable conditions can be readily determined by those having ordinary skill in the art based on, for example, the length and/or base composition of the polynucleotide. Conditions for hybridization can be of moderate or high stringency. For example, stringent conditions can include a prewashing solution containing 5×SSC, 0.5% SDS, 1.0 mM EDTA (pH 8.0), hybridization buffer of about 50% formamide, 6×SSC, and a hybridization temperature of about 55° C. for RNA-RNA hybridization (or about 50% formamide, with a hybridization temperature of about 42° C. for DNA-DNA hybridization), and washing conditions of about 60° C., in 0.5×SSC. 0.1% SDS. Generally, highly stringent conditions are defined as hybridization conditions as above, but with washing at approximately 68° C., 0.2×SSC, 0.1% SDS. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of reactions and duplex stability, as know to those skilled in the art and described further below.

When hybridizing a nucleic acid to a target polynucleotide of unknown sequence. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 12° C. less than the melting temperature (Tm) of the hybrid, where Tm is determined according to the following equations. For hybrids less than 18 base pairs in length, Tm (° C.)=2(# of A+T bases)+4(# of G+C bases). For hybrids above 18 base pairs in length. Tm (° C.)=$81.5+16.6(\log_{10}[Na^+])+0.41$ (% G+C)−(600/N), where N is the number of bases in the hybrid, and $[Na^+]$ is the concentration of sodium ions in the hybridization buffer ([Na+] for 1×SSC=0.165 M).

"Identity" refers to a comparison between pairs of nucleic acid or amino acid molecules. Methods for determining sequence identity are known. An exemplary, preferred computer program is the Genetics Computer Group (GCG; Madison, Wis.) Wisconsin package version 10.0 program, 'GAP' (Devereux et. al., 1984. *Nucl. Acids Res.* 12: 387; Smith and Waterman, 1981, *Adv. Appl. Math.* 2:482-489). The preferred default parameters for the 'GAP' program includes: (I) The GCG implementation of a unary comparison matrix (containing a value of 1 for identities and 0 for non-identities) for nucleotides, and the weighted amino acid comparison matrix of Gribskov and Burgess. *Nucl. Acids Res.* 14:6745, 1986, as described by Schwartz and Dayhoff, eds., *Atlas of Polypeptide Sequence and Structure*, National Biomedical Research Foundation, pp. 353-358, 1979; or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps.

"Isolated" refers to a polynucleotide or polypeptide that has been separated from at least one contaminant (polynucleotide or polypeptide) with which it is normally associated. For example, an isolated polynucleotide or polypeptide is in a context or in a form that is different from that in which it is found in nature.

"JAK2" refers to a member of the Janus family of tyrosine kinases known, among other things, to form complexes with cytokine receptor subunits, modulate the signal transducers and activators of transcription (STATs) signaling pathway, and be involved in regulating metabolic events within target cells (Carter-Su et al., 1998, *Recent Prog. Horm. Res.* 53:61-83). Illustrative techniques for determining tyrosine kinase activity are found in *Current Protocols in Molecular Biology*, Ausubel et al., eds. (Wiley & Sons, New York, 1988, and quarterly updates).

"Nucleic acid sequence" refers to the order or sequence of deoxyribonucleotides along a strand of deoxyribonucleic acid. The order of these deoxyribonucleotides determines the order of amino acids along a polypeptide chain. The deoxyribonucleotide sequence thus codes for the amino acid sequence.

"Polynucleotide" refers to a linear sequence of nucleotides. The nucleotides may be ribonucleotides, or deoxyribonucleotides, or a mixture of both. Examples of polynucleotides in the context of the present invention include single and double stranded DNA, single and double stranded RNA, and hybrid molecules having mixtures of single and double stranded DNA and RNA. The polynucleotides of the present invention may contain one or more modified nucleotides.

"Protein," "peptide," and "polypeptide" are used interchangeably to denote an amino acid polymer or a set of two or more interacting or bound amino acid polymers.

"Purify," or "purified" refers to a target protein that is free from at least 5-10% of contaminating proteins. Purification of a protein from contaminating proteins can be accomplished using known techniques, including ammonium sulfate or ethanol precipitation, anion or cation exchange chromatography, phosphocellulose chromatography, hydrophobic interaction chromatography, affinity chromatography, hydroxylapatite chromatography, and lectin chromatography. Various protein purification techniques are illustrated in *Current Protocols in Molecular Biology*, Ausubel et al., eds. (Wiley & Sons, New York. 1988, and quarterly updates).

"Selectable marker" refers to a marker that identifies a cell as having undergone a recombinant DNA or RNA event. Selectable markers include, for example, genes that encode antimetabolite resistance such as the DHFR protein that confers resistance to methotrexate (Wigler et al. (1980), Proc Natl Acad Sci USA 77: 3567-3570; O'Hare et al. (1981). Proc Natl Acad Sci USA, 78: 1527-1531), the GPT protein that confers resistance to mycophenolic acid (Mulligan & Berg (1981), Proc Natl Acad Sci USA, 78: 2072-2076), the neomycin resistance marker that confers resistance to the aminoglycoside G-418 (Calberre-Garapin et al. (1981), J Mol Biol 150:1-14), the Hygro protein that confers resistance to hygromycin (Santerre et al. (1984), Gene 30: 147-156), and the Zeocin™ resistance marker (Invitrogen). In addition, the herpes simplex virus thymidine kinase, hypoxanthine-guanine phosphoribosyltransferase and adenine phosphoribosyltransferase genes can be employed in tk⁻, hgprt⁻ and aprt⁻ cells, respectively.

"STAT5" refers to a member of the signal transducers and activators of transcription (STAT) family of transcription factors known to become activated by the JAK kinases, translocate to the nucleus, and participate in transcriptional regulation by binding to specific DNA sites. Illustrative techniques for determining STAT5 activity can be accomplished through any number of well known techniques, including DNA binding assays, STAT5 dependent reporter assays, $^{32}$P-labeling of STAT5, and the like, as illustrated in *Current Protocols in Molecular Biology*, Ausubel et al., eds. (Wiley & Sons, New York, 1988, and quarterly updates).

"Stringency" refers to the conditions (temperature, ionic strength, solvents, etc) under which hybridization between polynucleotides occurs. A hybridization reaction conducted under high stringency conditions is one that will only occur between polynucleotide molecules that have a high degree of complementary base pairing (85% to 100% identity). A hybridization reaction conducted under moderate stringency conditions is one that will occur between polynucleotide molecules that have an intermediate degree of complementary base pairing (50% to 84% identity) (Sambrook, J., E. F. Fritsch, and T. Maniatis 1989, *Molecular Cloning: A Laboratory Manual*, Cold Spring Harbor Laboratory Press, Cold Spring Harbor, N.Y., chapters 9 and 11; and *Current Protocols in Molecular Biology*, F. M. Ausubel et al., eds., John Wiley & Sons, Inc., sections 2.10 and 6.3-6.4).

"ULBP" refers to a family of MHC class 1-related molecules having a characteristic organization that includes a N-terminal signal sequence, centrally located alpha-1 and alpha-2 domains and a C-terminal cell membrane association domain (Table 3). ULBP family members are ligands for the effector cell receptor, NKG2D/DAP10, and are known to activate NK cells. As used herein. "ULBP polypeptide" includes active variants and fragments having NK cell activating activity. ULBP family members appear to elicit at least some of their effects on NK cells by activating JAK2, STAT5, ERK MAP kinase, and Akt/PKB (Sutherland et al., June 2001. *Immunol. Rev.* 181:185-192.).

"Variant", as used herein, means a polynucleotide or polypeptide molecule that differs from a reference molecule. Variants can include nucleotide changes that result in amino acid substitutions, deletions, fusions, or truncations in the resulting variant polypeptide when compared to the reference polypeptide. As used herein, "splicing variant" refers to a polynucleotide produced through alternative splicing of a precursor polynucleotide to yield a transcript having discrete portions of the precursor polynucleotide sequence removed.

"Vector," "extra-chromosomal vector" or "expression vector" refers to a first polynucleotide molecule, usually double-stranded, which may have inserted into it a second polynucleotide molecule, for example a foreign or heterologous polynucleotide. The heterologous polynucleotide molecule may or may not be naturally found in the host cell, and may be, for example, one or more additional copy of the heterologous polynucleotide naturally present in the host genome. The vector is adapted for transporting the foreign polynucleotide molecule into a suitable host cell. Once in the host cell, the vector may be capable of integrating into the host cell chromosomes. The vector may optionally contain additional elements for selecting cells containing the integrated polynucleotide molecule as well as elements to promote transcription of mRNA from transfected DNA and translation of a protein from the mRNA. Examples of vectors useful in the methods of the present invention include, but are not limited to plasmids, bacteriophages, cosmids, retroviruses, and artificial chromosomes.

ULBP Family

The ULBP family of ligands is a group of cell-surface receptors expressed on a wide range of cells, tissues, and tumors, including tumor tissue and immune tissue (Cosman et al., 2001, supra). ULBP1, ULBP2, and ULBP3 share 55% to 60% amino acid sequence identity, and like other MHC Class 1 related cell-surface proteins, possess alpha-1 and alpha-2 structural domains. Unlike traditional MHC class 1 related cell-surface proteins, the ULBPs lack an alpha-3 domain and, therefore, do not associate with beta-2 microglobulin. Each of ULBP1, ULBP2, and ULBP3 is glycosylphosphatidylinositol (GPI)-linked to the cell membrane, as compared to the transmembrane bound MHC class 1 proteins. The ULBPs are a family of MHC class 1 related ligands involved in modifying immune effector cell activity, particularly NK and T cell activity. ULBP proteins are expressed on many, but not all, tumor cell lines and cells from a variety of tissues. Cosman et al., supra. Infections can upregulate expression of NKG2D ligands. For example, bacterial infection can upregulate expression of MICA, an NKG2D ligand. Das et al. (2001). Immunity 15: 83-93; Tieng et al. (2002), Proc. Natl. Acad. Sci. 99(5): 2977-82. Although ULBPs are similar to the MHC Class 1 antigens, they have a function in immune surveillance that is similar to the non-traditional MHC Class 1 related antigens. MICA and MICB. Treatment of NK cells with soluble, trimeric forms of ULBP1, ULBP2, or ULBP3 stimulates NK cell production of IFN-gamma, GM-CSF, TNF-alpha. TNF-beta, and the chemokines MIP1-alpha, MIP1-beta, and 1-309 (Cosman (2001), Immunity 14: 123-133, Kubin et al., supra). In addition, the combination of IL-12 with a ULBP family member has a superadditive effect on GM-CSF and TNF-beta production, and a strong synergistic effect on 1-309 production.

ULBP family members transduce a dominant stimulatory signal to NK cells, overcoming inhibitory signals generated by the MHC class 1 engagement to NK expressed KIRs. ULBP family members are central actors in activating NK cells and are involved in stimulating other immune cells having the NKG2D/DAP10 receptor complex, for example T cells and activated macrophages. Ultimately, ULBP proteins are useful in therapies and treatments targeted at stimulating immune effector cells, for example, NK cells, to eliminate bacteria, virally infected cells, and tumor cells, as well as to stimulate NK cells to produce cytokines and chemokines that activate other immune system effector cells. Inhibition of ULBP expression or engagement of NKG2D receptors, for example by an anti-ULBP antibody, non-active ULBP fragment, ULBP oligomer, or inhibitory analog of ULBP, can inhibit NK cell activation. Inhibition of NK cell activation is therapeutically useful, for example, to reduce immune response to organ transplant and in the treatment of autoimmune disease.

ULBP4

As described more fully in the Examples below. ULBP4, a novel ULBP family member, has now been isolated and purified. The predicted amino acid sequence of ULBP4 (SEQ ID NO:2) has an organization that is characteristic of the ULBP family of proteins. Like ULBP1, ULBP2, and ULBP3, the ULBP4 polypeptide possesses a signal sequence, centrally located alpha-1 and alpha-2 domains, and C-terminal membrane association motif. The native ULBP4 contains a transmembrane binding domain, rather than the GPI domain found in ULBP1, ULBP2, and ULBP3. Like ULBP1, ULBP2, and ULBP3, the ULBP4 polypeptide lacks the alpha-3 domain found in traditional MHC class 1 molecules. ULBP4, as shown below, also binds known ULBP ligands (see Example 3). These structural and functional features identify ULBP4 as a member of the ULBP family of proteins.

ULBP polypeptides are expressed on numerous target cells and bind and activate the NKG2D/DAP10 receptor complex located on NK cells, as well as other immune system effector cells such as CD8+ αβT cells and γδ T cells. Binding of ULBP to the NKG2D/DAP10 complex activates the JAK2, STAT5, ERK MAP kinase, and Akt signal transduction pathways (Sutherland et al. (2001), supra). Activation of these pathways results in the activation of NK cells. Ultimately, ULPB activation of NK cells stimulates NK cell cytotoxicity toward the ULBP expressing cells. In addition, ULBP activation of NK cell production of cytokines and chemokines bolsters the immune response to viral infections and tumor surveillance (Cosman et al., 2001 supra). Like the other members of the ULBP family, the novel ULBP4 of the present invention binds to the NK cell stimulatory receptor complex, NKG2D/DAP10. ULBP4, via binding to NKG2D receptors on immune effector cells including NK cells, T cells, and macrophages, provides a stimulatory signal to the effector cells to induce production of cytokines and chemokines, and to induce target cell killing, particularly of tumor cells and infected cells.

ULBP4 Polypeptides

ULBP4 polypeptides of the invention include isolated polypeptides having an amino acid sequence as shown below in Example 1 [SEQ ID NO:2], as well as variants and derivatives, including fragments, having substantial identity to the amino acid sequence of SEQ ID NO:2 and that retain any of the functional activities of ULBP proteins such as binding to UL16 and/or to NKG2D receptors. ULBP polypeptide activity can be readily determined, for example, by subjecting the variant, derivative, or fragment of ULBP to a binding assay as described below in Example 3.

As shown below in Example 2. Table 3, the isolated ULBP4 polypeptide includes an N-terminal hydrophobic region that functions as a signal peptide, having an amino acid sequence that is predicted to begin with Met1, and terminates at an amino acid in the range of Ala23 to Ser32, optionally at Gly30. The remainder of the protein contains an alpha-1 domain having an amino acid sequence which begins at about His31 of SEQ ID NO:2 or at other amino acids from Leu24 to Ser 32 of SEQ ID NO:2 and extends to approximately Asp116; followed by an alpha-2 domain, that begins at approximately amino acid Pro117 and extends to about Thr207; and then a transmembrane domain, beginning at about amino acid Trp227 and extending to about amino acid Trp248, followed by a C-terminal tail. ULBPs 1-3 do not have the predicted transmembrane domain, but instead have a glycosylphosphatidylinositol (GPI) anchor signal motif, which links these molecules to the cell membrane via bound GPI. Derivatives of ULBP4 include, for example, ULBP4 polypeptides modified by covalent or aggregative conjugation with other chemical moieties, such as glycosyl groups, polyethylene glycol (PEG) groups, lipids, phosphate, acetyl groups, and the like, and ULBP4 polypeptides having terminal deletions.

The amino acid sequence of the ULBP4 polypeptides of the invention is optionally at least about 92% identical, at least about 93% identical, at least about 94% identical, at least about 95% identical, at least about 96% identical, at least about 97% identical, at least about 98% identical, or at least about 99% identical to the ULBP4 amino acid sequence shown above in Table 1 and SEQ ID NO:2. The percentage identity, also termed homology (see definition above) can be readily determined, for example, by comparing the two polypeptide sequences using any of the computer programs commonly employed for this purpose, such as the GAP program (Wisconsin Sequence Analysis Package, Version 8 for UNIX. Genetics Computer Group (GCG). University Research Park. Madison. Wis.), which uses the algorithm of Smith and Waterman, 1981. *Adv. Appl. Math.* 2:482-489. The preferred default parameters for the 'GAP' program for comparing proteins includes: (1) the weighted amino acid comparison matrix of Gribskov and Burgess, *Nucl. Acids Res.* 14:6745, 1986, as described by Schwartz and Dayhoff, eds., *Atlas of Polypeptide Sequence and Structure*, National Biomedical Research Foundation, pp. 353-358, 1979, or other comparable comparison matrices; (2) a penalty of 30 for each gap and an additional penalty of 1 for each symbol in each gap for amino acid sequences; (3) no penalty for end gaps; and (4) no maximum penalty for long gaps. Other programs used by those skilled in the art of sequence comparison can also be used.

The ULBP polypeptides of the present invention are preferably provided in an isolated form, and preferably are substantially purified. The polypeptides may be recovered and purified from recombinant cell cultures by known methods, including, for example, ammonium sulfate or ethanol precipitation, anion or cation exchange chromatography, phosphocellulose chromatography, hydrophobic interaction chromatography, affinity chromatography, hydroxylapatite chromatography, lectin chromatography, and/or high performance liquid chromatography (HPLC).

Variants

ULBP4 polypeptide variants within the scope of the invention can contain conservatively substituted amino acids, meaning that one or more amino acid can be replaced by an amino acid that does not alter the secondary and/or tertiary structure of the polypeptide. Such substitutions can include the replacement of an amino acid, by a residue having similar physicochemical properties, such as substituting one aliphatic residue (Ile, Val, Leu, or Ala) for another, or substitutions between basic residues Lys and Arg, acidic residues Glu and Asp, amide residues Gin and Asn, hydroxyl residues Ser and Tyr, or aromatic residues Phe and Tyr. Phenotypically silent amino acid exchanges are described more Fully in Bowie et al. ((1990), Science 247: 1306-1310). In addition, functional ULBP4 polypeptide variants include those having amino acid substitutions, deletions, or additions to the amino acid sequence outside functional regions of the protein, for example, outside the alpha-1 and alpha-2 domains.

ULBP1, ULBP2, ULBP3, and ULBP4 can be aligned to reveal amino acids common to all four proteins. See Table 3 below. One of skill in the art will realize that conserved amino acids among proteins with similar biological function and similar overall structure are more likely to be important for biological function than amino acids that are not conserved. Examples of such conserved amino acids include, for example, positions 44, 49, 50, 61, 62, 64, 77, 84, 87, and 94 of the ULBP4 sequence. Tee Table 3 below. Alteration of non-conserved residues, especially conservative alteration, is thus more likely to produce biologically functional variants than is alteration of conserved residues. Further, alterations predicted to substantially disturb the three dimensional structure of ULBP4 would also be likely to disturb biological function. Therefore alterations in non-conserved amino acids that do not substantially disturb the predicted three dimensional structure of ULBP4 are most likely to produce biologically functional variants. Three dimensional structure can be assessed by analyzing an amino acid sequence with a protein threading program that overlays a query amino acid sequence onto structural representatives of the Protein Data Bank. Jaroszewski et al. (1998), Pro. Sci. 7: 1431-40. One such protein threading program is GeneFold (Tripos. Inc., St. Louis, Mo.; Berman et al. (2000). Nucleic Acids Res. 28: 235-42).

Modification of the amino acid sequence of ULBP4 polypeptides can be accomplished by any of a number of known techniques. For example, mutations may be introduced at particular locations by oligonucleotide-directed mutagenesis (Walder et al., (1986), Gene 42: 133-139; Bauer et al. (1985), Gene 37: 73-81; Smith et al. *Genetic Engineering: Principles and Methods*, Plenum Press, (1981); and U.S. Pat. No. 4,518,584; and U.S. Pat. No. 4,737,462).

ULBP4 polypeptides, including variants and fragments, can be at least 20 amino acids long, optionally at least 30, 40, 50, 60, 70, 80, 100, 120, 130, 140, 160, 180, 200, or 220 amino acids long.

It is possible that some forms of ULBP proteins, including ULBP1, ULBP2, ULBP3, and/or UBLP4 fragments, variants, and/or fusion proteins, can be ULBP antagonists. Such a ULBP antagonist can block or inhibit the effects of a normal, activating ULBP protein. For example, an antagonistic form of a ULBP protein may block or inhibit the activation of immune effector cells by ULBP proteins capable of activating NK cells. Such an antagonist may function by binding to NKG2D in such a way that the inflammatory signal normally resulting from such binding does not occur. Such a bound, antagonistic ULBP protein may block access of other, activating ligands to NKG2D, thus resulting in an inhibition of the effects of these ligands. Alternatively, an antagonistic form of a ULBP protein may block or inhibit immune effector cell activation by ULBP proteins by binding to NKG2D and thereby causing NKG2D to become internalized without activating the immune effector cell.

Fusion Proteins

Variants and derivatives of the ULBP4 polypeptide include, for example, soluble ULBP4 polypeptides, as well as fusion proteins formed of a ULBP4 polypeptide (including ULBP4 fragments and variants) and a heterologous polypeptide. Heterologous polypeptides include those that facilitate purification, oligomerization, stability, or secretion of the ULBP4 polypeptides. Other heterologous polypeptides include targeting moieties that facilitate delivery of ULBP4 to a cell or tissue and polypeptide moieties that facilitate an immune effector cell response by, for example, attracting or activating the immune effector cell.

Fusion proteins of the invention contain a ULBP polypeptide linked to a heterologous polypeptide. The heterologous polypeptide can confer a functional characteristic to the fusion protein, such as stability, detection, targeting, and the like.

ULBP4 polypeptides can be fused to heterologous polypeptides to facilitate purification. Many available heterologous peptides (peptide tags) allow selective binding of the fusion protein to a binding partner. Non-limiting examples of peptide tags include 6-His, thioredoxin, hemaglutinin. GST, and the OmpA signal sequence tag. A binding partner that recognizes and binds to the heterologous peptide can be any molecule or compound, including metal ions (for example, metal affinity columns), antibodies, antibody fragments, or any protein or peptide that preferentially binds the heterologous peptide to permit purification of the fusion protein.

ULBP4 polypeptides can be modified to facilitate formation of ULBP4 oligomers. For example, ULBP4 polypeptides can be fused to peptide moieties that promote oligomerization, such as, for example, leucine zippers and certain antibody fragment polypeptides, for example, Fc polypeptides. A peptide moiety promotes oligomerization if, when fused to another protein, it causes the formation of dimers, trimers, and/or higher order oligomers. Techniques for preparing these fusion proteins are known, and are described, for example, in WO 99/31241 and in Cosman et al. ((2001). Immunity 14: 123-133). Fusion to an Fc polypeptide offers the additional advantage of facilitating purification by affinity chromatography over Protein A or Protein G columns. Fusion to a leucine-zipper (LZ), for example, a repetitive heptad repeat, often with four or five leucine residues interspersed with other amino acids, is described in Landschultz et al. ((1988). Science. 240: 1759).

ULBP polypeptides, including ULBP1, ULBP2, ULBP3, and/or ULBP4, can be modified for targeted cell delivery. For example. ULBP polypeptides can be fused to a ligand that binds a specific tumor cell antigen such as Her2, CEA, MUC-1, and the like, or a specific virally infected cell antigen such as CD. The ligand can be, for example, an antibody that specifically binds the cellular antigen, for example anti-Her2 antibody and the like. A molecule comprising a ULBP polypeptide, such as a ULBP1, UBLP2, ULBP3, or ULBP4 polypeptide, and a ligand that binds a specific tumor cell antigen, can further comprise a cytokine that can act as a chemoattractant and/or an activator of an cell expressing NKG2D. Such a molecule may attract NKG2D-expressing cells to tumor cells and increase the cytolytic activity of NKG2D-expressing cells. For example, a fusion protein comprising a ULBP polypeptide, an antibody that binds a tumor cell-specific antigen, and IL-15 can stimulate NK cells to kill tumor cells via both the ULBP polypeptide and IL-15.

Fusion proteins of the invention also include those containing anti-ULBP antibodies (as defined herein) linked to a therapeutic agent. In this embodiment, the anti-ULBP antibody serves as a cell targeting moiety to deliver the attached therapeutic agent to a ULBP-expressing cell. Such fusion proteins are useful, for example, to deliver cytotoxins and the like to tumor cells and virus-infected cells.

Fragments

Useful fragments of ULBP, including ULBP4, are those polypeptides having sufficient ULBP activity, such as the ability to bind NKG2D receptors and/or to activate NK cells. For example, a fragment lacking the transmembrane domain renders the ULBP polypeptide soluble, and retains activity. A soluble ULBP4 polypeptide may be produced, for example, by deleting all or a portion of the transmembrane domain, the amino acid sequence Trp227 to Trp248 shown in Table 2 and in SEQ ID NO:2. Such a fragment can begin at a position from amino acid 1 to amino acid 35 of SEQ ID NO:2 and end between amino acid 207 and amino acid 224 of SEQ ID NO:2. Optionally, such a fragment ends between amino acid 207 and 218, optionally at amino acid 217. A fragment can begin at approximately amino acid 31 or 32 of SEQ ID NO:2 and end at approximately amino acid 217 of SEQ ID NO:2. For recombinant production of such fragments, the ULBP4 signal sequence can be used, or a heterologous signal sequence can be used to facilitate secretion.

Fragments of the ULBP4 polypeptide can be used, for example, to generate specific anti-ULBP4 antibodies. Using known selection techniques, specific epitopes can be selected and used to generate monoclonal or polyclonal antibodies. Such antibodies have utility in assaying of ULBP4 activity, as well as in blocking or inhibiting ULBP4 activation of NKG2D receptors and immune effector cell activity of cells expressing NKG2D. Such anti-ULBP antibodies can be used to target therapeutic agents, such as cytotoxins or radioisotopes, to ULBP4-expressing cells, such as tumor cells.

Antibodies

The polypeptides of the present invention, in whole or in part, may be used to raise polyclonal and monoclonal antibodies that are useful in diagnostic assays for detecting ULBP4 polypeptide expression, as a reagent tool for characterizing the molecular actions of the ULBP4 polypeptide, in a quality control assay for a commercial process for production of a ULBP4 protein, and/or as a therapeutic agent. Anti-ULBP4 antibodies can bind specifically ULBP4 proteins. Specificity of binding can be tested in a number of ways including competitive displacement. For example, a non-radioactive ULPB4 protein, but not a non-radioactive protein that does not bind specifically an anti-ULBP4 antibody that binds specifically to ULBP4, can displace radioactive ULBP4 bound to the specifically-binding anti-ULBP4 antibody. In contrast, an unrelated protein combined with radioactive ULBP4 protein can have little effect on the amount of radioactive ULBP4 bound by a specifically-binding anti-ULBP4 antibody. Antibodies to ULBP polypeptides, including ULBP4, may be useful as therapeutic agents, for example, for the treatment of autoimmune diseases, tumors, infections, and diseases characterized by inappropriate inflammation, such as inflammatory bowel disease. All or part of the ULBP polypeptide can be used to generate antibodies. In particular, a polypeptide containing a unique epitope of the ULBP polypeptide, such as, for example, the 15 amino acids of the C-terminus of ULBP4, can be used in preparation of antibodies using conventional techniques. Methods for the selection of peptide epitopes and production of antibodies are known. See e.g., *Antibodies: A Laboratory Manual*, Harlow and Land (eds.), 1988. Cold Spring Harbor Laboratory Press, Cold Spring Harbor, N.Y.; *Monoclonal Antibodies, Hybridominas: A New Dimension in Biological Analyses*, Ken net et al. (eds.), 1980, Plenum Press, New York. In one embodiment, anti-ULBP antibodies can be fused to therapeutic agents (such as, for example, toxins and/or radioactive compounds) to facilitate delivery of the agents to ULBP-expressing cells. Some anti-ULBP4 antibodies can interfere with or antagonize the interaction between ULBP4 and NKG2D. Such antibodies can, for example, inhibit the enhancement of NK cell, T cell, and/or macrophage mediated cytotoxicity by cells that express ULBP4 or by a soluble ULBP polypeptide. Such an antibody is referred to herein as an antagonistic antibody. Such antibodies can be particularly appropriate as therapeutic agents for treating autoimmune diseases. Other anti-ULBP4 antibodies can bind ULBP4 without interfering with the interaction between UBLP4 and NKG2D.

Both polyclonal and monoclonal antibodies can be elicited by epitopes of the polypeptides of the invention, whether the epitopes have been isolated or remain pall of the polypeptides, and can be prepared by conventional techniques. See e.g., *Monoclonal Antibodies, Hybridomas: A New Dimension in Biological Analyses*, Kennet et al. (eds.), (1980) Plenum Press, New York; *Antibodies: A Laboratory Manual*, Harlow and Land (eds.), (1988) Cold Spring Harbor Laboratory Press, Cold Spring Harbor, N.Y.; Kohler and Milstein, U.S. Pat. No. 4,376,110; "The Human B-Cell Hybridoma Technique," (Kozbor et al. (1984), J. Immunol. 133: 3001-05); Cole et al. (11983), Proc. Natl. Acad. Sci. USA 80: 2026-30; and "The EBV-hybridoma technique," (Cole et al., in *Monoclonal Antibodies And Cancer Therapy*, Alan R. Liss, Inc., pp. 77-96 (1985)). Hybridoma cell lines that produce monoclonal antibodies specific for the polypeptides of the invention are also contemplated herein. Such hybridomas can be produced and identified by conventional techniques. The hybridoma producing the mAb of this invention can be cultivated in vitro or in vivo. Such monoclonal antibodies can be of any immunoglobulin class including IgG, IgM, IgE, IgA, IgD, and any subclass thereof.

In addition, techniques developed for the production of "chimeric antibodies" (Takeda et al. (1985), Nature 314:452-454; Morrison et al. (1984), Proc Natl Acad Sci USA 81:6851-6855; Boulianne et al. (1984), Nature 312: 643-646; Neuberger et al. (1985), Nature 314: 268-70) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a porcine mAb and a human immunoglobulin constant region.

The monoclonal antibodies of the present invention also include humanized versions of murine monoclonal antibodies. Such humanized antibodies can be prepared by known techniques and offer the advantage of reduced immunogenicity when the antibodies are administered to humans. Procedures for the production of chimeric and further engineered monoclonal antibodies include those described in Riechmann et al., ((1988). Nature 332:323), Liu et al. ((1987), PNAS 84: 3439), Larrick et al. ((1989), BioTechnology 7:934), and Winter and Harris ((1993), 1TIPS 14:139). Useful techniques for humanizing antibodies are also discussed in U.S. Pat. No. 6,054,297.

Procedures to generate antibodies transgenically, particularly human antibodies generated in a transgenic non-human animal, can be found in GB 2,272,440, U.S. Pat. Nos. 5,569,825 and 5,545,806, and related patents. Preferably, for use in humans, the antibodies are human or humanized; techniques for creating such human or humanized antibodies are also well known and are commercially available from, for example, Medarex Inc. (Princeton, N.J.) and Abgenix Inc. (Fremont, Calif.). In another preferred embodiment, fully human antibodies for use in humans are produced by screening a phage display library of human antibody variable domains. Vaughan et al. (1998), Nat. Biotechnol. 16(6): 535-539; and U.S. Pat. No. 5,969,108.

Antigen-binding antibody fragments which recognize specific epitopes can be generated by known techniques. For example, antibody fragments include but are not limited to the F(ab')$_2$ fragments which can be produced by pepsin digestion of the antibody molecule and the antibody fragments which can be generated by reducing the disulfide bridges of the F(ab')$_2$ fragments. Alternatively, Fab expression libraries can be constructed (Huse et al. (1989), Science 246:1275-1281) to allow rapid, useful and easy identification of monoclonal Fab fragments with the desired specificity. The term "antibody" is used here in the broadest sense and specifically includes both native and mutant forms, single monoclonal antibodies, antibody compositions with polyepitopic specificity, as well as antibody fragments (e.g., Fab, F(ab')$_2$, Fv, Fc) that exhibit the desired biological activities. Forms of the Fc region of an antibody that contain one or more of the Fc region's $C_H$ domains, including truncated forms of Fc polypeptides containing the dimerization-promoting hinge region (Fc or Fc polypeptide), and particularly Fc polypeptides derived from human IgG1 antibody are useful in the ULBP fusion proteins of the invention.

Techniques described for the production of single chain antibodies (U.S. Pat. No. 4,946,778; Bird (1988), Science 242: 423-426; Huston et al. (1988), Proc. Natl. Acad. Sci. USA 85: 5879-5883: and Ward et al. (1989), Nature 334: 544-546) can also be adapted to produce single chain antibodies against ULBP gene proteins. Single chain antibodies are formed by linking the heavy and light chain fragments of the Fv region via an amino acid bridge, resulting in a single chain polypeptide. Such single chain antibodies can also be useful intracellularly (i.e., as intrabodies), for example, as described by Marasco et al. ((1999), J. Immunol. Methods 231: 223-238,) for genetic therapy in HIV infection. In addition, antibodies to the ULBP polypeptide can, in turn, be utilized to generate anti-idiotype antibodies that "mimic" the ULBP polypeptide and that may bind to the ULBP polypeptide's binding partners using techniques well known to those skilled in the art. (See, e.g., Greenspan & Bona (1993). FASEB J 7(5): 437-444; and Nissinoff (1991), J. Immunol. 147(8): 2429-2438). Such antibodies can also find use in methods for detecting and quantitating anti-ULBP4 antibodies. Further, such anti-idiotype antibodies can, for example, bind to NKG2D and may or may not activate immune effector cells expressing NKG2D. Thus such antibodies may activate NKG2D-expressing immune effector cells, including NK cells, T cells, and/or macrophages, or may block or inhibit activation of such cells via NKG2D.

Antibodies that bind specifically with the polypeptides of the invention include bispecific antibodies (i.e. antibodies that are immunoreactive with the polypeptides of the invention via a first antigen binding domain, and also immunoreactive with a different polypeptide via a second antigen binding domain). A variety of bispecific antibodies have been prepared, and found useful both in vitro and in vivo (see, for example, U.S. Pat. No. 5,807,706; and Cao and Suresh (1998), Bioconjugate Chem 9: 635-644). Further, tetravalent, bispecific molecules can be prepared by fusion of DNA encoding the heavy chain of an F(ab')$_2$ fragment of an antibody with either DNA encoding the heavy chain of a second F(ab')$_2$ molecule (in which the $C_H1$ domain is replaced by a $C_H3$ domain), or with DNA encoding a single chain FV fragment of an antibody, as described in U.S. Pat. No. 5,959,083. Bispecific antibodies can also be produced as described in U.S. Pat. No. 5,807,706. Moreover, single-chain variable fragments (sFvs) have been prepared by covalently joining two variable domains: the resulting antibody fragments can form dimers or trimers, depending on the length of a flexible linker between the two variable domains. Kortt et al. (1997), Protein Engineering 10:423-433.

A peptibody, such as a peptibody that binds to a ULBP protein, including ULBP1, ULBP2, ULBP3, and ULBP4, can be used in lieu of an antibody in any of the therapeutic uses for antibodies discussed herein. Peptibodies are described in WO 01/83525 and WO 00/24782.

Polynucleotide Sequences

The invention also provides polynucleotide molecules encoding the ULBP4 polypeptides discussed above. ULBP polynucleotides molecules of the invention include the following molecules: polynucleotide molecules having the nucleic acid sequence shown in Table 1 and SEQ ID NO:1; polynucleotide molecules that hybridize under highly or moderately stringent conditions to the nucleic acid sequence of Table 1 and SEQ ID NO:1; and polynucleotide molecules having substantial nucleic acid sequence identity with the nucleic acid sequence of Table 1 and SEQ ID NO:1, particularly with those nucleic acids encoding the alpha-1 and alpha-2 domains of the ULBP4 polypeptide, having an amino acid sequence beginning with either Leu24. His31, Ser32, or an amino acid between Leu24 and Ser32 and extending to approximately Thr207, His217 or to an amino acid from Thr207 to His217 Such polynucleotides include a region starting at from residue 70 to residue 94 of SEQ ID NO:1 and ending at from residue 621 to residue 651 of SEQ ID NO:1.

Useful ULBP4 polynucleotide molecules of the invention are preferably isolated molecules encoding the ULBP4 polypeptide having an amino acid sequence as shown in Table 1 and SEQ ID NO:2, as well as derivatives, variants, and useful fragments of the ULBP4 polynucleotide. The ULBP4 polynucleotide sequence can include deletions, substitutions, or additions to the nucleic acid sequence of Table 1 and SEQ ID NO:1.

The ULBP4 polynucleotide molecule of the invention can be cDNA, chemically synthesized DNA, DNA amplified by PCR, RNA, or combinations thereof. Due to the degeneracy of the genetic code, two DNA sequences may differ and yet encode identical amino acid sequences. The present invention thus provides an isolated polynucleotide molecule having a nucleic acid sequence encoding ULBP4 polypeptide, where the nucleic acid sequence encodes a ULBP4 polypeptide having the complete amino acid sequences as shown in Table 1 and SEQ ID NO:2, or variants, derivatives, and fragments thereof.

The ULBP4 polynucleotides of the invention have a nucleic acid sequence that is at least 92% identical to the nucleic acid sequence shown in Table 1 and SEQ ID NO:1. Optionally, the nucleic acid sequence is at least 93%, at least 94%, at least 95%, at least 96%, at least 97%, at least 98%, or at least 99% identical to the nucleic acid sequence shown in Table 1 and SEQ ID NO:1. The percent identity of two nucleic acid sequences can be determined by visual inspection and mathematical calculation, or more preferably, the comparison is done by comparing sequence information using a computer program. An exemplary, preferred computer program is the Genetics Computer Group (GCG; Madison, Wis.) Wisconsin package version 10.0 program, 'GAP' (Devereux et al., 1984, *Nucl. Acids Res.* 12: 387). The preferred default parameters for the 'GAP' program includes: (1) The GCG implementation of a unary comparison matrix (containing a value of 1 for identities and 0 for non-identities) for nucleotides or other comparable comparison matrices; (2) a penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used, such as, for example, the BLASTN program version 2.0.9 or the UW-BLAST 2.0 algorithm. Alternatively, nucleic acid sequence identity is determined by known methods, for example by aligning two sequences in a software program such as the MACAW program created by Greg Schuler (Schuler et al., 1991 *Proteins* 9: 180-190).

The ULBP4 polynucleotide molecules of the invention also include isolated polynucleotide molecules having a nucleic acid sequence that hybridizes under high stringency conditions (as defined above) to the nucleic acid sequence shown in Table 1 and SEQ ID NO:1. Hybridization of the polynucleotide is to at least 15 contiguous nucleotides, preferably to at least 20 contiguous nucleotides, and more preferably to at least 30 contiguous nucleotides, and still more preferably to at least 100 contiguous nucleotides of the nucleic acid sequence shown in Table 1 and SEQ ID NO:1.

Useful fragments of the ULBP4-encoding polynucleotide molecules described herein, include probes and primers. Such probes and primers can be used, for example, in PCR methods to amplify and detect the presence of ULBP4 polynucleotides in vitro, as well as in Southern and Northern blots for analysis of ULBP4. Cells expressing the ULBP4 polynucleotide molecules of the invention can also be identified by the use of such probes. Methods for the production and use of such primers and probes are known. For PCR. 5' and 3' primers corresponding to a region at the termini of the ULBP4 polynucleotide molecule can be employed to isolate and amplify the ULBP4 polynucleotide using conventional techniques. One exemplary hybridization probe or primer comprises nine or more contiguous nucleic acids taken from the unique 3' transmembrane region of ULBP4:

[SEQ ID NO: 9]
GAG TGG CAG GCT GGT CTC TGG CCC TTG AGG ACG TCT
TAG

Other useful fragments of the ULBP4 polynucleotides include antisense or sense oligonucleotides comprising a single-stranded nucleic acid sequence capable of binding to a target ULBP4 mRNA (using a sense strand), or DNA (using an antisense strand) sequence.

Still other useful nucleic acids include interfering RNAs (which can be double-stranded RNAs including sequence from a ULBP mRNA), or sequences encoding interfering RNAs (which include DNAs that encode RNA haripins comprising sequences from a ULBP mRNA), that can inhibit expression of ULBP proteins. See e.g. Bosher and Labouesse (2000), Nature Cell Biol. 2: E31-E36; Fjose et al. (2001), Biotechnol. Ann. Rev. 7: 31-57.

Vectors and Host Cells

The present invention also provides vectors containing the polynucleotide molecules of the invention, as well as host cells transformed with such vectors. Any of the polynucleotide molecules of the invention including one or more of ULBP1, ULBP2, ULBP3, and ULBP4 may be contained in a vector, which generally includes a selectable marker and an origin of replication, for propagation in a host. The vectors further include suitable transcriptional or translational regulatory sequences, such as those derived from a mammalian, microbial, viral, or insect genes, operably linked to the ULBP polynucleotide molecule. Examples of such regulatory sequences include transcriptional promoters, operators, or enhancers, mRNA ribosomal binding sites, and appropriate sequences that control transcription and translation. Nucleotide sequences are operably linked when the regulatory sequence functionally relates to the DNA encoding the target protein. Thus, a promoter nucleotide sequence is operably linked to a ULBP DNA sequence if the promoter nucleotide sequence directs the transcription of the ULBP sequence.

Selection of suitable vectors for the cloning of ULBP4 polynucleotide molecules encoding the target ULBP4 polypeptides of this invention will depend upon the host cell in which the vector will be transformed, and, where applicable, the host cell from which the target polypeptide is to be expressed. Suitable host cells for expression of ULBP4 polypeptides include prokaryotes, yeast, and higher eukaryotic cells, each of which is discussed below.

The ULBP polypeptides to be expressed in such host cells may also be fusion proteins that include regions from heterologous proteins. As discussed above, such regions may be included to allow, for example, secretion, improved stability, facilitated purification, targeting, or oligomerization of the ULBP polypeptide. For example, a nucleic acid sequence encoding an appropriate signal peptide can be incorporated into an expression vector. A nucleic acid sequence encoding a signal peptide (secretory leader) may be fused in-frame to a ULBP sequence so that ULBP is translated as a fusion protein comprising the signal peptide. A signal peptide that is functional in the intended host cell promotes extracellular secretion of the ULBP polypeptide. A heterologous signal peptide can replace the native signal sequence. Examples of signal peptides that are functional in mammalian host cells include the signal sequence for interleukin-7 (IL-7) described in U.S. Pat. No. 4,965,195, the signal sequence for interleukin-2 receptor described in Cosman et al. ((1984), Nature 312: 768); the interleukin-4 receptor signal peptide described in EP Patent No. 0 367 566; the type 1 interleukin-1 receptor signal peptide described in U.S. Pat. No. 4,968,607; the type II interleukin-1 receptor signal peptide described in EP Patent No. 0 460 846; the signal sequence of human IgK (which is METDTLLLWVLLLWVPGSTG (SEQ ID NO:10)); and the signal sequence of human growth hormone (which is MATGSRTSLLLAFGLLCLPWLQEGSA (SEQ ID NO:11)). Preferably, the signal sequence will be cleaved from the ULBP polypeptide upon secretion of ULBP from the cell, Other signal sequences that can be used in practicing the invention include the yeast α-factor and the honeybee melatin leader in Sf9 insect cells. Brake (1989), Biotechnology 13: 269-280; Homa et al. (1995). Protein Exp. Purif. 6141-148; Reavy et al. (2000), Protein Exp. Purif. 6: 221-228.

Suitable host cells for expression of target polypeptides of the invention include prokaryotes, yeast, and higher eukaryotic cells. Suitable prokaryotic hosts to be used for the expression of these polypeptides include bacteria of the genera *Escherichia, Bacillus*, and *Salmonella*, as well as members of the genera *Pseudomonas, Streptomyces*, and *Staphylococcus*. For expression in prokaryotic cells, for example, in *E. coli*, the polynucleotide molecule encoding ULBP polypeptide preferably includes an N-terminal methionine residue to facilitate expression of the recombinant polypeptide. The N-terminal Met may optionally be cleaved from the expressed polypeptide.

Expression vectors for use in cellular hosts generally comprise one or more phenotypic selectable marker genes. Such genes encode, for example, a protein that confers antibiotic resistance or that supplies an auxotrophic requirement. A wide variety of such vectors are readily available from commercial sources. Examples include pGEM vectors (Promega), pSPORT vectors, and pPROEX vectors (InVitrogen, Life Technologies, Carlsbad, Calif.), Bluescript vectors (Stratagene), and pQE vectors (Qiagen).

ULBP can also be expressed in yeast host cells from genera including *Saccharomyces, Pichia*, and *Kluveromyces*. Preferred yeast hosts are *S. cerevisiae* and *P. pastoris*. Yeast vectors will often contain an origin of replication sequence from a 2μ yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*. Direct secretion of the target polypeptides expressed in yeast hosts may be accomplished by the inclusion of nucleotide sequence encoding the yeast α-factor leader sequence at the 5' end of the ULBP-encoding nucleotide sequence. Brake (1989), Biotechnology 13: 269-280.

Insect host cell culture systems can also be used for the expression of ULBP polypeptides. The target polypeptides of the invention are preferably expressed using a baculovirus expression system, as described, for example, in the review by Luckow and Summers ((1988), BioTechnology 6: 47).

ULBP polypeptides of the invention can be expressed in mammalian host cells. Non-limiting examples of suitable mammalian host cell lines include the COS-7 line of monkey kidney cells (Gluzman et al. (1981), Cell 23: 175-182), Chinese hamster ovary (CHO) cells (Puck et al. (1958), PNAS USA 60: 1275-1281), CV-1 (Fischer et al. (1970), Int. J. Cancer 5: 21-27) and human cervical carcinoma cells (HELA) (ATCC CCL 2).

The choice of a suitable expression vector for expression of ULBP polypeptides of the invention will depend upon the specific mammalian host cell to be used. Examples of suitable expression vectors include pcDNA3.1/Hygro⁺ (invitrogen), pDC409 (McMahan et al. (1991), EMBO J. 10: 2821-2832), and pSVL (Pharmacia Biotech). Expression vectors for use in mammalian host cells can include transcriptional and translational control sequences derived from viral genomes. Commonly used promoter sequences and enhancer sequences that can be used to express ULBP4 include, but are not limited to those derived from human cytomegalovirus (CMV), Adenovirus 2, Polyoma virus, and Simian virus 40 (SV40). Methods for the constriction of mammalian expression vectors are disclosed, for example, in Okayama and Berg ((1982) *Mol. Cell. Biol.* 2:161-170), Cosman et al. ((1986) Mol. Immunol. 23:935-941), Cosman et al. ((1984) Nature 312: 768-771), EP-A-0367566, and WO 91/18982.

Modification of a ULBP polynucleotide molecule to facilitate insertion into a particular vector (for example, by modifying restriction sites), ease of use in a particular expression system or host (for example, using preferred host codons), and the like, are known and are contemplated for use in the invention. Genetic engineering methods for the production of ULBP polypeptides include the expression of the polynucleotide molecules in cell free expression systems, in cellular hosts, in tissues, and in animal models, according to known methods.

Pharmaceutical Compositions

The invention provides pharmaceutical compositions containing a substantially purified ULBP polypeptide of the invention, including fragments, variants, and/or fusion proteins, or an antibody that immunospecifically binds to such ULBP polypeptides, and a pharmaceutically acceptable carrier. Such pharmaceutical compositions are administered to cells, tissues, or patients, for a variety of purposes including: to induce the activity of NKG2/DAP10-expressing cells, including NK cells, T cells (including αβ T cells and γδ T cells), and activated macrophages; to induce the production of cytokines and chemokines; to induce cytotoxicity of immune effector cells against tumor cells and infected cells such as virally or bacterially infected cells; and for therapeutic treatment, for example, of cancer, viral infection, and bacterial infection. A ULBP polypeptide can be a fusion protein, for example, fused to a targeting moiety.

The invention also provides reagents, compositions, and methods that are useful for analysis of NK and/or T cell activity; for analysis of NKG2D receptor engagement and activation; and for analysis of the inhibitory/stimulatory effects of signal molecules involved in the innate immune system response to infection and to neoplastic cells.

ULBP polynucleotides and polypeptides, including vectors expressing ULBP, of the invention can be formulated as pharmaceutical compositions and administered to a host, preferably mammalian host, including a human patient, in a variety of forms adapted to the chosen route of administration. The compounds are preferably administered in combination with a pharmaceutically acceptable carrier, and may be combined with or conjugated to specific delivery agents, including targeting antibodies and/or cytokines.

ULBP can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques that are well known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes. More preferably, the compounds of the present invention are administered parenterally, i.e. injected intravenously, intraarterially, intramuscularly, intralesionally, subcutaneously, or intraperitoneally by infusion or injection. Localized administration, that is, at the site of disease, is contemplated, as are transdermal delivery and sustained release from implants or skin patches. In one embodiment of the invention, the compounds may be administered directly to a tumor by injection; or by systemic delivery by intravenous injection. Other alternatives include eyedrops, oral preparations such as pills, lozenges, syrups, and chewing gum, and topical preparations such as lotions, gels, sprays, and ointments. In most cases, therapeutic molecules that are polypeptides can be administered topically or by injection or inhalation.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. The ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin.

Sterile injectable solutions are prepared by incorporating the compounds in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Dosage

The therapeutic dosing and regimen most appropriate for patient treatment will vary with the disease or condition to be treated, and according to the patient's weight and other parameters. A useful dose of a ULBP polypeptide or an antibody against a ULBP polypeptide can be about 0.01-100 mg ULBP/kg/day (or less, see below) administered systemically. It is expected that much smaller doses, e.g., in the 0.001-1 mg ULBP/kg/day range with longer duration of treatment, will also produce therapeutically useful results.

Doses can be administered at any appropriate frequency and for any appropriate duration. For example, doses can be administered daily, every other day, once every three days, twice per week, once per week, once every ten days, once every two weeks, once every three weeks, once per month, or once every two months, among many possible dosing regimens. The frequency and/or amount of each dose need not remain constant throughout the duration of treatment. Treatment may continue for any appropriate duration from one or more days to years.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Factors include the size of the patient, the age of the patient, the general condition of the patient, the particular disease being treated, the severity of the disease, the presence of other drugs in the patient, and the like. The trial dosages would be chosen after consideration of the results of animal studies and the clinical literature.

Assays

Agents that modify, for example, increase or decrease, ULBP stimulation of NK cells, or other cells that express NKG2D such as $CD8^+$ $\alpha\beta$ T cells, $\delta\gamma$ T cells, or macrophages, can be identified, for example, by assay of ULBP binding to the NKG2D/DAP10 receptor and/or analysis of ULBP/NKG2D complex formation, of NK cell or T cell mediated cytotoxicity, or of NK cell or T cell production of chemokines and/or cytokines. Incubation of NK cells in the presence of a ULBP4 polypeptide and in the presence or absence of a test agent and correlation of ULBP/NKG2D complex formation, of NK cell or T cell mediated cytotoxicity, or of NK cell or T cell production of chemokines and/or cytokines with ULBP4 activity or inhibition permits screening of such agents. In such assays, a disproportionate decrease or increase in the NKG2D receptor-mediated activity of ULBP-treated cells versus an untreated control is correlated with the test agent's stimulation or inhibition of ULBP4 activity.

Specific target activities for ULBP polypeptide, including ULBP4, in NKG2D expressing cells (NK cells, or T cells, or macrophages), for example, ULBP activation of the anti-apoptotic serine/threonine kinase Akt, PKB, JAK2 tyrosine kinase, as well as the STAT5 transcription factor, and ERK map kinase can also be analyzed and correlated with activity versus inhibition of a test agent.

Preferably, a soluble form of ULBP is used to stimulate the ULBP target activity in NKG2D expressing cells. Optionally, the NKG2D expressing cells can be NK cells. The ULBP4 stimulated activity is determined in the presence and absence of a test agent and then compared. A lower ULBP4 activated test activity in the presence of the test agent, than in the absence of the test agent, indicates that the test agent has decreased the activity of the ULBP. A higher ULBP activated test activity in the presence of the test agent than in the absence of the test agent indicates that the test agent has increased the activity of the ULBP. Stimulators and inhibitors of ULBP may be used to augment, inhibit, or modify ULBP mediated activity, and therefore may have potential therapeutic uses. For example, inhibitors of ULBP may be useful to reduce NK cell cytotoxicity, for example in autoimmune diseases or in patients undergoing organ transplants.

Therapeutic Applications

The ULBP polypeptides, including the ULBP4 polypeptides of the invention, are effective NK cell, T cell, and/or macrophage activating agents. In the methods of the invention, the immune effector cell activating effects of ULBP polypeptides are achieved by treating immune effector cells with picomolar to millimolar amounts of the ULBP polypeptide, and preferably with nanomolar or micromolar amounts of soluble ULBP polypeptide. Activated NK cells have been shown to lyse bacteria, lyse virus-infected cells, and participate in the elimination of tumor cells. See for example. Whiteside et al. (1996), Anticancer Res. 16(4C): 2537-64; Yamaue et al. (1989), Cancer Immunol Immunother. 29(2): 79-86. ULBP stimulation of NK cells produces cytokines and chemokines that activate other components of the immune system and is therefore useful as a treatment in viral infections or bacterial infections and in certain types of tumor cell treatments. Cells other than NK cells that also express the ULBP receptor NKG2D, such as $CD8^+$ $\alpha\beta$ T cells and $\gamma\delta$ T cells can also be activated by NKG2D ligands. Diefenbach et al. (2000), Nature Immunology 1(2): 119-26: Bauer et al. (1999), Science 285: 727-29.

(1) Cytokine/Chemokine Production

Isolated, and preferably purified. ULBP polypeptides, including ULBP1, ULBP2, ULBP3, and/or ULBP4, may be used to stimulate production of cytokines and chemokines from cells, such as NK cells, $CD8^+$ $\alpha\beta$ T cells, macrophages, and/or $\gamma\delta$ T cells. Optionally, ULBP polypeptides used in this method are fused to a LZ or Fc moiety as discussed above, creating a ULBP-LZ fusion protein, which can be a multimer such as a trimer or a dimer, or a ULBP-Fc fusion protein, which can be a multimer such as a dimer. Primary NK cells are treated with IL-15 or other like material for a period of time, preferably from 15 to 20 hours, to maximize ULBP binding to the NK cells. Treated cells are then stimulated with a soluble ULBP polypeptide, preferably at a concentration of from about 0.05 to about 20.0 μg/ml, optionally from about 0.5 to about 5.0 μg/ml or from about 0.8 to about 3.0 μg/ml. The stimulated cells are further incubated for period of time, preferably from about 15 to 20 hours, and the supernatant is collected. Cytokines and chemokines are isolated and purified from the supernatant by conventional methods. Cytokines and chemokines produced via ULBP-induced activation of cells, such as NK cells, include GM-CSF, interferon γ, TNF-alpha, TNF-beta, MIP1-alpha, MIP1-beta and CC chemokine 1-309. The IL-15 treated NK cells are optionally stimulated with a combination of soluble ULBP4 and IL-12 to achieve even greater yield.

(2) Treatment of Tumors and Infections

The ULBP polypeptides, including ULBP4 variants; fragments, and fusion proteins, also Find utility as therapeutic agents for the treatment of tumors and infections, for example bacterial or viral infections. Accordingly, the present invention encompasses methods for inhibiting or halting tumor growth, killing tumor cells, or reducing the size and/or number of tumors in a patient. The invention further encompasses methods for treating a viral or bacterial infection by administering to an individual a ULBP polypeptide. Treatment of an infection, which may be a viral or bacterial infection or an infection by a eukaryotic organism, encompasses: a reduction of the amount of detectable infective particles or organisms; a reduction in the amounts of detectable nucleic acids or proteins of the infective virus or organism; and/or a reduction in the symptoms associated with the infection.

Cancer or infections can be treated by administering a soluble ULBP polypeptide, which may be a variant, fragment, and/or fusion protein, that can bind to NKG2D and activate cells that express NKG2D, preferably NK cells, T cells, and/or macrophages. Alternatively, such conditions can be treated by administering an anti-idiotypic antibody that can bind to an anti-ULBP antibody, which is capable of binding to NKG2D and activating cells that express NKG2D. In cases where a cancer or an infection expresses a ULBP protein, the cancer or infection can be treated using an antibody that specifically binds to a ULBP protein. Binding of the antibody to a cancerous or infected cell can stimulate antibody-dependent cell-mediated cytotoxicity, leading to death of the cancerous or infected cell. Optionally, the antibody can be fused to a cytotoxic or radioactive agent to further enhance the cytotoxic effects of antibody binding.

Some, but not all, cancer cells express ULBP proteins. See e.g. Cosman et al., supra; Onda et al. (2001), Biochem. Biophys. Res. Comm. 285: 235-43. To increase the number of ULBP proteins localized near a cancer cell, which may or may not express a ULBP protein, a ULBP protein, including ULBP1, UBLP2, UBLP3, and/or ULBP4, can be fused to an antibody or other polypeptide (such as one selected in vitro to bind to a tumor antigen) that binds to a tumor-specific antigen and used to treat a tumor. Further, such a ULBP fusion protein can further include a cytokine, such as, for example. IL-15, IL-2, and/or IL-12, and this triple fusion protein can be used to treat cancers or infections. Cytokines fused to tumor-specific antibodies, in which both the cytokine and the antibody retain biological function, have been found to be effective anti-cancer agents in a variety of settings. See e.g. Gillies et al. (2002), Cancer Immunol. Immunother. 51: 449-60; Ruehlmann et al. (2001). Cancer Res. 61: 8498-503; Holden et al. (2001), Clinical Cancer Res. 7: 2862-69. The addition of a ULBP protein to a cytokine:antibody fusion can further stimulate immune response against tumor cells.

In still another embodiment, a method is provided for preventing or inhibiting growth of tumor cells that remain in a patient subsequent to surgery for removal of a tumor. Nucleic acid encoding a ULBP protein, including ULBP1, ULBP2, ULBP3, and/or ULBP4 and fragments, variants, and/or fusions thereof, can be introduced into cultured tumor cells derived from a tumor was surgically removed from a patient. These cells can then be treated so as to prevent further proliferation, for example, by irradiating them. Such non-dividing cells having a ULBP protein expressed on their surface can be re-introduced into the patient from whom they were removed. Such cells can serve as a vaccine that can raise an immune response against tumor cells of the same type as those surgically removed. Such a treatment may prevent or inhibit growth of tumor cells that remain in a patient after surgery.

(3) Anti-ULBP Antibodies as Targeting Moieties

Anti-ULBP antibodies, including anti-ULBP4 antibodies, can be therapeutically useful to target ULBP-expressing cells, including tumor cells or infected cells, for destruction by the immune system through antibody-dependent cell-mediated cytotoxicity, complement fixation, or other mechanisms. In addition, anti-ULBP antibodies can be fused to cytotoxic, cytostatic, or radioactive agents, can be therapeutically useful to target these therapeutic agents to ULBP-expressing cells, such as tumor cells or cells infected by virus, bacteria, or eukaryotic organisms. Alternatively, anti-ULBP4 antibodies fused to radioactive or luminescent agents can be used to detect ULBP4-expressing cells. Numerous cytotoxic, cytostatic, luminescent, or radioactive agents are known in the art and have been fused to other antibodies to halt growth of cells, to kill cells, or to detect cells expressing particular antigens. Examples of such agents include: maytansine derivatives (such as DM1), enterotoxins (such as a Staplilyococcal enterotoxin), iodine isotopes (such as iodine-125), technetium isotopes (such as Tc-99m), cyanine fluorochromes (such as Cy5.5.18), or ribosome-inactivating proteins (such as bouganin, gelonin, or saporin-S6). On administration, fusion proteins containing an anti-ULBP antibody and a desired cytotoxic, cytostatic, luminescent, or radioactive agent bind to the target ULBP expressing cell, thus allowing its detection or carrying the therapeutic agent to the cell to in order to kill the cell or inhibit its proliferation. If a tumor cell expresses ULBP4, for example, such a targeting moiety can be used to kill the tumor cell or prevent its proliferation.

(4) Synergy with IL-12

ULBP proteins and IL-12 synergize strongly to induce interferon-gamma production from NK cells pretreated with IL-15. ULBP proteins also upregulate mRNA levels for chemokines. In particular, the chemokines 1-309 and lymphotactin were shown to be upregulated by the ULBP proteins. Additionally, in NK cells, cytokines that are known markers of NK cell activation, including GM-CSF, lymphotoxin-alpha and TNF-alpha are upregulated on administration of ULBP. As discussed above. NK cells are capable of exerting a cytotoxic effect by lysing a variety of cell types. Thus, a host system's ability to activate NK cells and target the activated NK cell to an infected cell or tumor cell is an important feature in fighting infection and tumors.

(5) Binding to NKG2D/Dap 10

As described and demonstrated below by way of an Example, the ULBP polypeptides, including ULBP4, bind to NKG2D/Dap10, an antigen expressed by NK cells, CD8$^+$ αβ T cells, γδ T cells, and in some macrophages. Activation of NK killer cells results in production of cytokines and induction of NK cell killing. The ability of the ULBP proteins to synergize in the production of key cytokines indicates that the ULBP proteins can activate NK cell cytolytic function. Accordingly, ULBP proteins find utility as anti-tumor therapeutics and as therapeutics to treat infections, including viral or bacterial infections or infections by eukaryotic organisms, including protozoans.

Moreover, bifunctional molecules or multifunctional molecules, that are able to bind and activate NK cells, macrophages, γδ T cells, or CD8$^+$ αβ T cells and also bind tumor cells are useful in accordance with the present invention. Suitable bifunctional or multifunctional molecules may be molecules that include at least one ULBP protein, or NKG2D-receptor binding fragment of a ULBP protein, and, a polypeptide or other moiety that binds a tumor cell antigen, such as, for example, a single chain antibody. It can be appreciated that such a therapeutic is capable of binding to and activating NK cells, macrophages, γδ T cells, and/or CD8+ αβ T cells and targeting tumor cells for lysis by these effector cells.

(6) Immunosuppression

In addition, agents that interfere with the ability of ULBPs to activate the immune system are useful in situations where down-modulation of an immune response is desired, such as transplantation (Manilay et al., 1998, Curr. Opin. Immunol. 10:532-538), graft versus host disease, graft rejection, autoimmune disease, gene therapy (Hackett et al., 2000, Curr. Opin. Mol. Therap. 2:376-382), diseases characterized by inappropriate inflammation such as inflammatory bowel disease and Crohn's disease, and the like. For example, an antagonistic antibody or peptibody that binds specifically to a ULBP, including but not limited to ULBP1, ULBP2, ULBP3 and ULBP4, can be administered prior to, at approximately the same time (either shortly before or shortly after), or concurrently with administration of a gene therapy vector to a mammal, transplantation, or as otherwise appropriate for the desired immuno-suppression. Also appropriate for such a treatment is an antagonistic form of a ULBP polypeptide (including variants, fragments, and fusion proteins) or an anti-idiotypic antibody that can block or inhibit activation via NKG2D.

An antagonistic anti-ULBP antibody or an antagonistic form of a ULBP polypeptide or anti-idiotypic antibody can be administered to a patient suffering from an autoimmune disease in order to decrease the number of detectable autoantibodies, to decrease the activation of immune effector cells, and/or to decrease or eliminate the symptoms of the autoimmune disease. Autoimmune diseases include all conditions in which the patient's own tissues are subject to deleterious effects caused by the patient's immune system. Such effects can be mediated by autoantibodies and/or by the activation of immune effector cells, among other possibilities. Antagonizing NKG2D ligands, such as the ULBP proteins, can be particularly helpful where activation of immune effector cells plays a role in the disease pathology. Although the causes of autoimmune diseases are usually unclear, a correlation between the existence of various kinds of infections and various autoimmune diseases has been established in some cases and is a recurring subject of discussion in the scientific literature. See e.g. Corapcioglu et al. (2002). Thyroid 12: 613-17; Sewell et al. (2002), Immunol. Lett. 82: 101-10; Rose (1998), Semin. Immunol. 10(1): 5-13; Matsiota-Bernard (1996), Clin. Exp. Immunol. 104: 228-35; and McMurray and Elbourne (1997), Semin. Arthritis Rheum. 26: 690-701.

One of skill in the art will appreciate that symptoms of autoimmune diseases are extremely diverse and can depend on what tissues are targeted by the patients immune system. Autoimmune diseases can be organ-specific or systemic, including, for example, Addison's disease, insulin-dependent diabetes mellitus (type 1 diabetes mellitus), polyglandular endocrinopathy syndromes, systemic lupus erythematosus, chronic active hepatitis, various forms of thyroiditis (including Hashimoto's thyroiditis, transient thyroiditis syndromes, and Grave's disease), lymphocytic adenohypophysitis, premature ovarian failure, idiopathic phyoparathyroidism, pernicious anemia, glomerulonephritis, autoimmune neutropenia, Goodpasture's syndrome, multiple sclerosis, vitiligo, myasthenia gravis, rheumatoid arthritis, scleroderma, primary Sjogren's syndrome, polymyositis, autoimmune hemolytic anemia, autoimmune thrombocytopenic purpura, pemphigus vulgaris, acute rheumatic fever, mixed essential cryoglobulinemia, and warm autoimmune hemolytic anemia, among many others.

Further, an antagonistic anti-ULBP antibody or peptibody or an antagonistic ULBP polypeptide or anti-idiotypic antibody can be administered to a patient suffering from inflammatory diseases, such as inflammatory bowel disease and Crohn's disease, to decrease or eliminate the symptoms of these diseases.

In addition, in all of the above therapeutic applications for UBLPs, other ligands for NKG2D, known or yet to be discovered, can be substituted for ULBPs. These ligands include, but are not limited to, MICA, MICB, and antibodies and peptibodies that bind to NKG2D.

Within the application, unless otherwise stated, the techniques utilized may be found in any of several well-known references, such as: *Molecular Cloning: A Laboratory Manual*, Sambrook et al. (1989): "Gene Expression Technology," *Methods in Enzymology*, Vol. 185, edited by D. Goeddel, (1991) Academic Press, San Diego, Calif.: "Guide to Protein Purification" in *Methods in Enzymology*, M. P. Deutscher, 3d., (1990) Academic Press, Inc.; *PCR Protocols: A Guide to Methods and Applications* Innis et al. (1990) Academic Press, San Diego, Calif.: *Culture of Animal Cells: A Manual of Basic Technique*, 2nd ed., R. I. Freshney (1987) Liss, Inc., New York, N.Y.; and *Gene Transfer and Expression Protocols*, pp 109-128, ed. E. J. Murray. The Humana Press Inc., Clifton, N.J.

Having generally described the invention, the same will be more readily understood by reference to the following examples, which are provided by way of illustration and are not intended as limiting.

EXAMPLES

Example 1

Molecular Cloning of Human ULPB4 cDNA

Published cDNA sequences disclosed in two related patents, WO 99/06554 ('554) and WO 99/31236 ('236), were identified hereinas having possible homology to the ULBP family of proteins. WO '554 disclosed a 370 bp EST sequence, reported to likely encode a secretory protein, however, the EST was not recognized as encoding any specific protein, nor any protein related to any known family of proteins. WO '236 recited a 989 base pair sequence of extended cDNA [SEQ ID NO:320] believed to encode a portion of a human secretory protein. The sequence was not recognized as encoding any specific protein, nor any protein related to any known family of proteins.

A public genomic database (NCBI/NIH) was searched for sequences having homology to the 989 bp cDNA sequence of the WO '236 application. The search revealed a homologous, but non-identical, sequence on a genomic stretch of DNA (GenBank accession no. AL355312). Based on knowledge of the intron-exon structure of the ULBP1, 2, and 3 genes, the structure of the ULBP4 gene was predicted and used to design PCR primers that would be specific for a predicted ULBP4 cDNA. The two primers, forward primer: 5' TAT GTC GAC CTC CAC AGT ATG CGA AGA ATA TCC CTG 3' (SEQ ID NO:7) and reverse primer: 5'ATA GGC GGC CGC AGA CTA AGA CGT CCT CAA 3' (SEQ ID NO:8), were used to amplify a full length ULBP4 cDNA from a Namalwa (human B cell lymphoma) cDNA library (cell line CRL-1432 available from ATCC, Manassas, Va.) by PCR. A cDNA was cloned, sequenced, and found to have an 789 base pair open reading frame. The nucleic acid sequence of the cDNA clone (SEQ ID NO:1) and its deduced amino acid sequence (SEQ ID NO:2) are shown in Table 1.

TABLE 1

ULBP4

| Amino acid / Codon | Position |
|---|---|
| Met Arg Arg Ile Ser Leu Thr Ser Ser Pro Val Arg Leu Leu<br>ATG CGA AGA ATA TCC CTG ACT TCT AGC CCT GTG CGC CTT CTT | 14 |
| Leu Phe Leu Leu Leu Leu Leu Ile Ala Leu Glu Ile Met Val<br>TTG TTT CTG CTG TTG CTA CTA ATA GCC TTG GAG ATC ATG GTT | 28 |
| Gly Gly His Ser Leu Cys Phe Asn Phe Thr Ile Lys Ser Leu<br>GGT GGT CAC TCT CTT TGC TTC AAC TTC ACT ATA AAA TCA TTG | 42 |
| Ser Arg Pro Gly GLn Pro Trp Cys Glu Ala Gln Val Phe Leu<br>TCC AGA CCT GGA CAG CCC TGG TGT GAA GCG CAG GTC TTC TTG | 56 |
| Asn Lys Asn Leu Phe Leu Gln Tyr Asn Ser Asp Asn Asn Met<br>AAT AAA AAT CTT TTC CTT CAG TAC AAC AGT GAC AAC AAC ATG | 70 |
| Val Lys Pro Leu Gly Leu Leu Gly Lys Lys Val Tyr Ala Thr<br>GTC AAA CCT CTG GGC CTC CTG GGG AAG AAG GTA TAT GCC ACC | 84 |
| Ser Thr Trp Gly Glu Leu Thr Gln Thr Leu Gly Glu Val Gly<br>AGC ACT TGG GGA GAA TTG ACC CAA ACG CTG GGA GAA GTG GGG | 98 |
| Arg Asp Leu Arg Met Leu Leu Cys Asp Ile Lys Pro Gln Ile<br>CGA GAC CTC AGG ATG CTC CTT TGT GAC ATC AAA CCC CAG ATA | 112 |
| Lys Thr Ser Asp Pro Ser Thr Leu Gln Val Glu Met Phe Cys<br>AAG ACC AGT GAT CCT TCC ACT CTG CAA GTC GAG ATG TTT TGT | 126 |
| Gln Arg Glu Ala Glu Arg Cys Thr Gly Ala Ser Trp Gln Phe<br>CAA CGC GAA GCA GAA CGG TGC ACT GGT GCA TCC TGG CAG TTC | 140 |
| Ala Thr Asn Gly Glu Lys Ser Leu Leu Phe Asp Ala Met Asn<br>GCC ACC AAT GGA GAG AAA TCC CTC CTC TTT GAC GCA ATG AAC | 154 |
| Met Thr Trp Thr Val Ile Asn His Glu Ala Ser Lys Ile Lys<br>ATG ACC TGG ACA GTA ATT AAT CAT GAA GCC AGT AAG ATC AAG | 168 |
| Glu Thr Trp Lys Lys Asp Arg Gly Leu Glu Lys Tyr Phe Arg<br>GAG ACA TGG AAG AAA GAC AGA GGG CTG GAA AAG TAT TTC AGG | 182 |
| Lys Leu Ser Lys Gly Asp Cys Asp His Trp Leu Arg Glu Phe<br>AAG CTC TCA AAG GGA GAC TGC GAT CAC TGG CTC AGG GAA TTC | 196 |
| Leu Gly His Trp Glu Ala Met Pro Glu Pro Thr Val Ser Pro<br>TTA GGG CAC TGG GAG GCA ATG CCA GAA CCG ACA GTG TCA CCA | 210 |
| Val Asn Ala Ser Asp Ile His Trp Ser Ser Ser Leu Pro<br>GTA AAT GCT TCA GAT ATC CAC TGG TCT TCT TCT AGT CTA CCA | 224 |
| Asp Arg Trp Ile Ile Leu Gly Ala Phe Ile Leu Leu Val Leu<br>GAT AGA TGG ATC ATC CTG GGG GCA TTC ATC CTG TTA GTT TTA | 238 |
| Met Gly Ile Val Leu Ile Cys Val Trp Trp Gln Asn Gly Glu<br>ATG GGA ATT GTT CTC ATC TGT GTC TGG TGG CAA AAT GGT GAG | 252 |
| Trp Gln Ala Gly Leu Trp Pro Leu Arg Thr Ser<br>TGG CAG GCT GGT CTC TGG CCC TTG AGG ACG TCT TAG | [SEQ ID NO: 2]<br>[SEQ ID NO: 1] |

The amino acid sequence predicted by the cDNA was determined to have homology to the ULBP polypeptides as shown below in Example 2, Table 3. The novel ULBP polypeptide. ULBP4, has a predicted amino acid sequence that is distinct from that predicted from the cDNA sequence disclosed in WO 99/31236 [SEQ ID NO:320], with 26 non-identical amino acids out of 263, as shown in Table 2. Eight of the distinct amino acid residues fall within the approximately 183 amino acids of the alpha-1 and alpha-2 domains. Of these, two of the mismatched amino acids, those at positions 123 and 166, are represented by potential stop codons in the corresponding positions in the cDNA sequence disclosed in WO 99/31236 (SEQ ID NO:320).

TABLE 2

```
WO'236   1  MRRISLTSSPVRLLLXLLLLLIALEIMVGGHSLCFNFTIKSLSRPGQPWC  50
            |||||||||||||||| |||||||||||||||||||||||||||||||||
ULBP4    1  MRRISLTSSPVRLLLFLLLLLIALEIMVGGHSLCFNFTIKSLSRPGQPWC  50

51  EAHVFLNKNLFLQYNSDNNMVKPLGLLGKKVYATSTWGELTQTLGEVGRD 100
            ||:|||||||||||| ||||||||||||||||||||||||||||||||||
        51  EAQVFLNKNLFLQYNSDNNMVKPLGLLGKKVYATSTWGELTQTLGEVGRD 100

101  LRMLLCDIKPQIKTSDPSTLQVXXFCQREAERCTGASWQFATNGEKSLLF 150
            ||||||||||||||||||||||  ||||||||||||||||||||||||||
       101  LRMLLCDIKPQIKTSDPSTLQVEMFCQREAERCTGASWQFATNGEKSLLF 150

151  DAMNMTWTVINHEASXIKETWKKDRXLEXYFRKLSKGDCDHWLREFLGHW 200
            ||||||||||||||| ||||||||| || ||||||||||||||||||||
       151  DAMNMTWTVINHEASKIKETWKKDRGLEKYFRKLSKGDCDHWLREFLGHW 200

201  EAMPXPXVSPXNASXIHWSSSXLPXXWIILGAFILLXLMGIVLICVWWQN 250
            |||| | ||| ||| ||||||  ||  ||||||||| |||||||||||||
       201  EAMPEPTVSPVNASDIHWSSSSLPDRWIILGAFILLVLMGIVLICVWWQN 250

251  GXXSTXX*......  258  WO '236  [SEQ ID NO: 6]

251  GEWQAGLWPLRTS*  264  ULBP4    [SEQ ID NO: 2]
```

Example 2

ULBP4 is a Member of the ULBP Family

Sequence alignments and comparisons of the amino acid sequences of ULBP1, ULBP2, ULBP3, and ULBP4 polypeptides were prepared, using the PILEUP and GAP programs of the Genetics Computer Group, Inc (GCG, Inc., Madison, Wis.). An examination of the amino acid sequence alignment of the ULBP family members indicates that the amino acid sequence of ULBP4 is homologous to the amino acid sequences of know ULBP family members, ULBP1, ULBP2, and ULBP3 (See Table 3). The amino acid sequence predicted for ULBP4 is approximately 35% identical to ULBP1, approximately 28% identical to ULBP2, and approximately 33% identical to ULBP3.

In particular. ULBP4 has regions that are homologous to the alpha-1 and alpha-2 domains of ULBP1, ULBP2, and ULBP3. For example, the alpha-1 domain of the ULBP4 polypeptide extends from amino acid residues Leu24-His31 to Asp116. This closely conforms to the alpha-1 domain of ULBP1, ULBP2 and ULBP3. The alpha-2 domain of the ULBP4 polypeptide extends from amino acid residues Pro117 to Thr207, which closely conforms to the alpha-2 domain of ULBP1, ULBP2 and ULBP3. Highly conserved amino acid residues are present throughout the alpha-1 and alpha-2 domains, adding further support that ULBP4 is a member of the ULBP family. The alignment data supports a conclusion that ULBP4 is a member of this protein family.

A novel polynucleotide molecule and corresponding deduced polypeptide, ULBP4 is identified herein as a new member of the ULBP family of proteins. Several interesting features are present in the amino acid sequence of ULBP4, including a signal sequence, alpha-1 and alpha-2 domains, and a unique transmembrane domain with a short cytoplasmic tail. As discussed above, this structure is characteristic for the known ULBP polypeptides. ULBP1, ULBP2, and ULBP3. The novel ULPB4, like ULBP1, ULBP2, and ULBP3, differs from traditional MHC class 1 molecules in that it lacks an alpha-3 domain and is therefore unable to associate with beta-2 microglobulin.

TABLE 3

```
                        signal sequence
ULBP1  ~~~~~MAAAA  SPAFLLCLPL  L.HLLSGWSR  AGWV  DTHCLC  YDFIITPKSR
ULBP2  ~~~~~MAAAA  ATKILLCLPL  L.LLLSGWSR  AGRA  DPHSLC  YDITVIPKFR
ULBP3  ~~~~~MAAAA  SPAILPRLAI  LPYLLFDWSG  TGRA  DAHSLW  YNFTIIHLPR
ULBP4  MRRISLTSSP  VRLLLFLLLL  LIAL......  EIMV  GGHSLC  FNFTIKSLSR
       1                      *           **                  44

α1 domain
ULBP1  PEPQWCEVQG  LVDERPFLHY  DCVNHKAKAF  ASLGKKVNVT  KTWEEQTETL
ULBP2  PGPRWCAVQG  QVDEKTFLHY  DCGNKTVIPV  SPLGKKLNVT  TAWKAQNPVL
ULBP3  HGQQWCEVQS  QVDQKNFLSY  DCGSDKVLSM  GHLEEQLYAT  DAWGKQLEML
ULBP4  PGQPWCEAQV  FLNKNLFLQY  NSDNNMVKPL  GLLGKKVYAT  STWGELTQTL
       45                                                         94

ULBP1  RDVVDFLKGQ  LLDIQVENLIPIE   PLTLQAR  MSCEHEAHGH  GRGSWQFLFN
ULBP2  REVVDILTEQ  LRDIQLENYTPKE   PLTLQAR  MSCEQKAEGH  SSGSWQFSFD
ULBP3  REVGQRLRLE  LADTELEDFTPSG   PLTLQVR  MSCECEADGY  IRGSWQFSFD
ULBP4  GEVGRDLRML  LCDIK.PQIKTSD   PSTLQVE  MFCQREAERC  TGASWQFATN
       95                   113  117                              143

α2 domain
ULBP1  GQKFLLFDSN  NRKWTALHPG  AKKMTEKWEK  NRDVTMPFQK  ISLGDCKMWL
```

TABLE 3-continued

```
ULBP2  GQIFLLFDSE  KRMWTTVHPG  ARKMKEKWEN  DKVVAMSFHY  FSMGDCIGWL
ULBP3  GRKFLLEDSN  NRKWTVVHAG  ARRMKEKWEK  DSGLTTFFKM  VSMRDCKSWL
ULBP4  GEKSLLFDAM  NMTWTVINHE  ASKIKETWKK  DRGLEKYFRK  LSKGDCDHWL
       144                                            193

GPI anchor signal
ULBP1  EEFLMYWEQM  LDPT..  KPPS  LAPGTTQPKA  MATTLSPWSL  LIIFLCFILA
ULBP2  EDFLMGMDST  LEPSAG  APLA  MSSGTTQLRA  TATTLILCCL  LIILPCFILP
ULBP3  RDFLMHRKKR  LEPT..  APPT  MAPGLAQPKA  IATTLSPWSF  LIIL.CFILP
ULBP4  REFLGHWEAM  PEPT..  ..VS  PVNASDIHWS  SSSLPDRWII  LGAFILLVLM
                                                        ---TM domain--
       194                  211                         239

ULBP1  GR*~~~~~~  ~~~~~~~~~~  ~~~~                      [SEQ ID NO: 3]
ULBP2  GI*~~~~~~  ~~~~~~~~~~  ~~~~                      [SEQ ID NO: 4]
ULBP3  GI*~~~~~~  ~~~~~~~~~~  ~~~~                      [SEQ ID NO: 5]
ULBP4  GIVLICVWWQ  NGEWQAGLWP  LRTS*                    [SEQ ID NO: 2]
       ---------
       240                   263
```

Note:
Numbering is according to the amino acid sequence of ULBP4.
*Potential end of ULB4 signal sequence

Example 3

Binding of ULBP4 to NK Receptors

NKG2D cell surface receptors mediate ULBP activation of NK killer cells (Cosman et al. (2001), Immunity 14: 123-133). The ULBP4 polypeptide of Examples 1 and 2 was analyzed for its ability to bind CV-1 cells expressing recombinant NKG2D receptor, following the general methods described in Cosman et al., supra.

Fc fusion protein constructs expressing human and murine NKG2D-Fc were prepared, expressed in CV-1 cells, and the fusion proteins were purified from culture supernatants by chromatography (protein A-Poros column. PerSeptive Biosystems). The Fc fusion proteins contained the extracellular domain of the protein of interest fused to the amino terminus of the hinge region of a modified human IgG1 Fc region (Baum et al. (1994), EMBO J. 13: 3992-4001) and were subcloned into the mammalian expression vector pDC409 (Giri et al. (1994), EMBO J. 13: 2822-2830).

The UL16-Fc fusion protein contained the extracellular domain of UL16 fused to the Fc region after amino acid 183. The NKG2D-Fc fusion protein contained the extracellular region of the NKG2D fused to the Fc region at amino acid 74. These soluble fusion proteins were prepared as described (Cosman et al. (2001), Immunity 14: 123-133).

CV-1 cells were transfected with pDC409 vectors containing cDNA expressing full length ULBP1, ULBP2, ULBP3, and ULBP4, as well as an empty vector control. The transfected cells were then incubated with human or murine NKG2D-Fc or with UL16-Fc in phosphate buffered saline containing 3% fetal bovine serum. After incubation with the indicated fusion protein for 1 hour on ice, the cells were washed twice and incubated with goat anti-human IgG (Fc specific) antibody conjugated to phycoerythrin (PE) (Sigma, Milwaukee, Wis.). Cells were washed twice and analyzed for binding by flow cytometry in a Becton Dickinson FACScan. Cells that fluoresced between one log to two logs above background (background was taken as the amount of fluorescence from the cells stained with the second step reagent alone) were characterized as ++. Cells that fluoresced more strongly were scored as +++. Cells that fluoresced more than background, but less than one log above background, were characterized as +.

As shown below in Table 4, ULBP4 bound strongly and specifically to human NKG2D-Fc, in a pattern that was similar to the binding activity of ULBP3. Like each of ULBP1, ULBP2, and ULBP3, the novel protein ULBP4 bound to the human NK killer cell receptor, NKG2D. This binding activity, taken together with the high degree of structural identity with ULBP1, ULBP2, and ULBP3, confirms placement of ULBP4 in the ULBP family of proteins that stimulate immune effector cells via engagement of the NKG2D receptor.

TABLE 4

| Binding Results | | | |
|---|---|---|---|
| | Human NKG2D-Fc | Murine NKG2D-Fc | UL16-Fc |
| ULBP1 | +++ | +++ | +++ |
| ULBP2 | +++ | +++ | ++ |
| ULBP3 | +++ | Negative | Negative |
| ULBP4 | +++ | + | Negative |
| Empty 409 vector | Negative | Negative | Negative |

Example 4

Enhancement of NK Cell-Mediated Cytotoxicity by ULBP Proteins

This experiment was a $^{51}$Cr release assay designed to determine whether the expression of a ULBP protein on the surface of a $^{51}$Cr-labeled target cell can enhance killing of the target cell by an NK effector cell.

Human NK cells came from the human NK cell line NKL described in Robertson et al. ((1996), Exp. Hematol. 24:406-15). Murine NK cells were obtained from C57/B6 SCID mice as follows. The mice were sacrificed, and the spleens were removed and squashed to release cells, which consisted primarily of red blood cells. B cells. T cells, and NK cells. The released cells were incubated for 2 minutes at room temperature in 155 mM $NH_4Cl$, 16.5 mM Tris-HCl, pH 7.4 and promptly washed in medium in order to selectively lyse the red blood cells, leaving most of the other cells intact. To stimulate expansion of NK cells, the remaining cells were cultured for 3 days at 2 million cells per milliliter in medium containing 200 nanograms per milliliter of recombinant human IL-15 (described in U.S. Pat. No. 5,574,138, where IL-15 is called "epithelium-derived T-cell factor," and in EP 0 772 624). On day 3, cells were stained with an antibody that binds specifically to murine NKG2D, which is expressed on murine NK cells, to determine what percentage of the cells are NK cells. A culture in which at least about 80% of the cells stain with the antibody to murine NKG2D is suitable for use in a cytotoxicity assay on day 4.

The target cells were EL4 cells, a lymphoma cell line available from e.g. American Type Culture Collection, either not transfected or transfected with nucleic acids encoding the full length human ULBP1, ULBP2, ULBP3, or ULBP4 proteins. Untransfected EL4 cells do not express human ULBP1, ULBP2, ULBP3, or ULBP4 proteins. Target cells were fed $^{51}Cr$ in medium for about 1 hour and subsequently washed.

Assays were preformed in 96-well microtiter plates in a total volume of 200 μl. For human NK effector cells, $10^4$ target cells were incubated for 2 to 3 hours at 37° C. in 5% $CO_2$ with varying numbers of NK (i.e., effector) cells in the following effector:target cell ratios: 5:1, 2.5:1, 1.25:1, or 0.6:1. For murine NK effector cells, $5\times10^3$ target cells were incubated for 2 to 3 hours at 37° C. in 5% $CO_2$ with varying numbers of NK (i.e., effector) cells in the following effector:target cell ratios: 20:1, 10:1, 5:1, or 2.5:1. As a negative control, target cells were incubated without effector cells. As a positive control, target cells were lysed with detergent. Radioactivity released into the medium was counted in a gamma counter. Percent cytotoxicity was calculated as the released radioactivity of an experimental sample less the released radioactivity of the negative control divided by the released radioactivity of the positive control less the released radioactivity of the negative control multiplied by 100. Results are shown in FIGS. 1 and 2.

Figure 2:
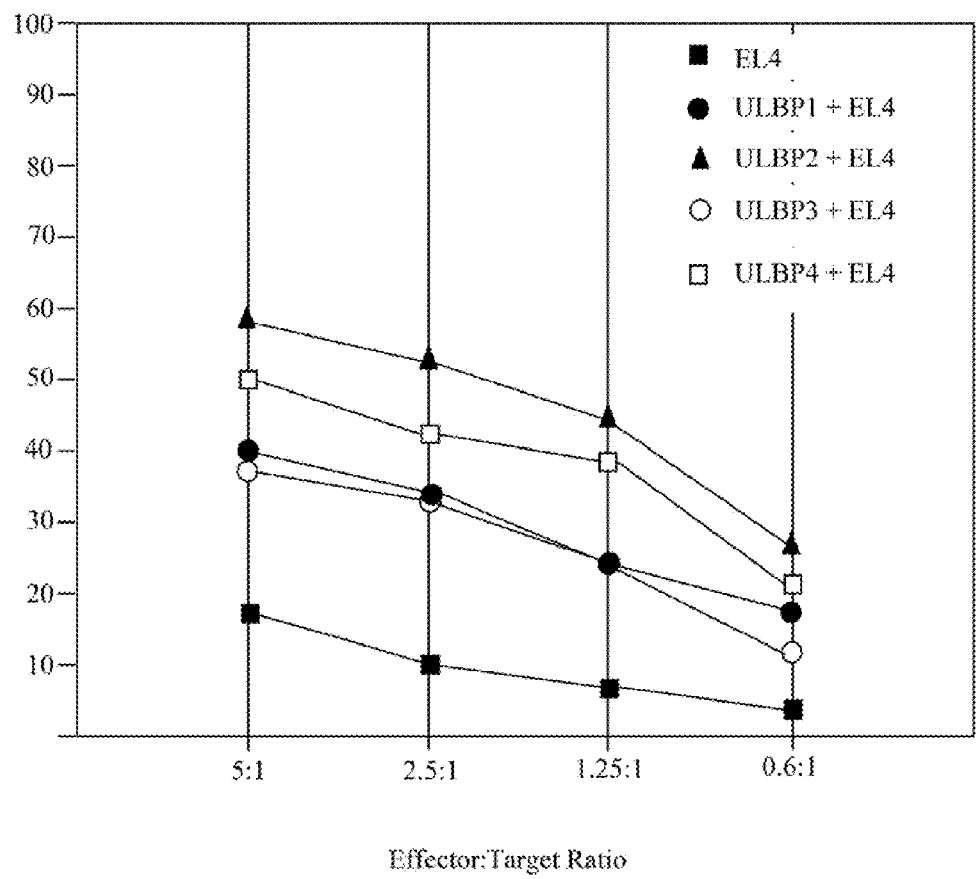
FIG. 2 shows the percent cytotoxicity of human NK cells (effector cells) when combined with target cells, either $^{51}$Cr-labeled untransfected EL4 cells or $^{51}$Cr-labeled EL4 cells that have been transfected with nucleic acids encoding the indicated ULBP protein, as a function of the effector cell:target cell ratio.

FIG. 1 indicates that the expression human ULBP1, ULBP2, or ULBP4 protein on the surface of the target cells can enhance the cytotoxicity of murine NK cells. FIG. 2 indicates that the expression of ULBP1, ULBP2, ULBP3, or ULBP4 protein on the surface of the target cells can enhance cytotoxicity of human NK cells.

Example 5

Binding of Soluble Forms of ULPB4 to NK Cells

The following experiment was done to determine whether soluble forms of human ULBP4 protein could bind to human NK cells.

Two different constructs encoding ULBP4:Fc fusion proteins were created. One encoded a ULBP4:Fc protein starting at position 1 and ending at position 217 of SEQ ID NO:2 (ULBP4:Fc-B). The other encoded a ULBP4 protein starting at position 1 and ending at position 224 of SEQ ID NO:2 (ULBP4:Fc-A). Both of these ULBP4 proteins were fused at their carboxy terminii to an Fc region of a human IgG1 antibody. These ULBP4:Fc fusion proteins, plus a ULBP1:FC fusion protein used as a control, were purified by Protein A chromatography from medium of mammalian cells transfected with constructs encoding the proteins. Analysis of the amino terminal sequence of these ULBP4 proteins indicated that His31 of SEQ ID NO:2 is the amino terminus of the mature form of these proteins.

Human NK cells were isolated from two different donors and stimulated overnight with recombinant human IL-15 as described in Kubin et al. ((2001), Eur. J. Immunol. 31: 1428-37). About one million NK cells were pre-incubated with 1 μg of protein (either ULBP4:Fc-A, ULBP4:Fc-B, or ULBP1:Fc) for 30 minutes at 0° C. The NK cells were subsequently washed, stained with an fluorescently-labeled antibody specific for the Fc region of a human IgG antibody, and analyzed by flow cytometry. As a negative control, NK cells not pre-incubated with any protein were washed, stained, and analyzed like the experimental samples. The mean fluorescence intensity of the samples using NK cells from one donor are shown in Table 5. Values using NK cells from the other donor are similar.

TABLE 5

| Pre-incubation protein | Mean fluorescence intensity |
|---|---|
| None | 6 |
| ULBP4:Fc-A | 10 |
| ULBP4:Fc-B | 20 |
| ULBP1:Fc | 35 |

These data show that ULBP4:Fc-B can bind to NK cells, while ULBP4:Fc-A binds to a lesser extent, if at all.

Example 6

ULBP-Mediated Rejection of Tumors in Wild Type Mice In Vivo

The following experiment tests whether expression of ULBP proteins on the surface of murine tumor cells can play a role in tumor rejection in vivo.

Figure 3:
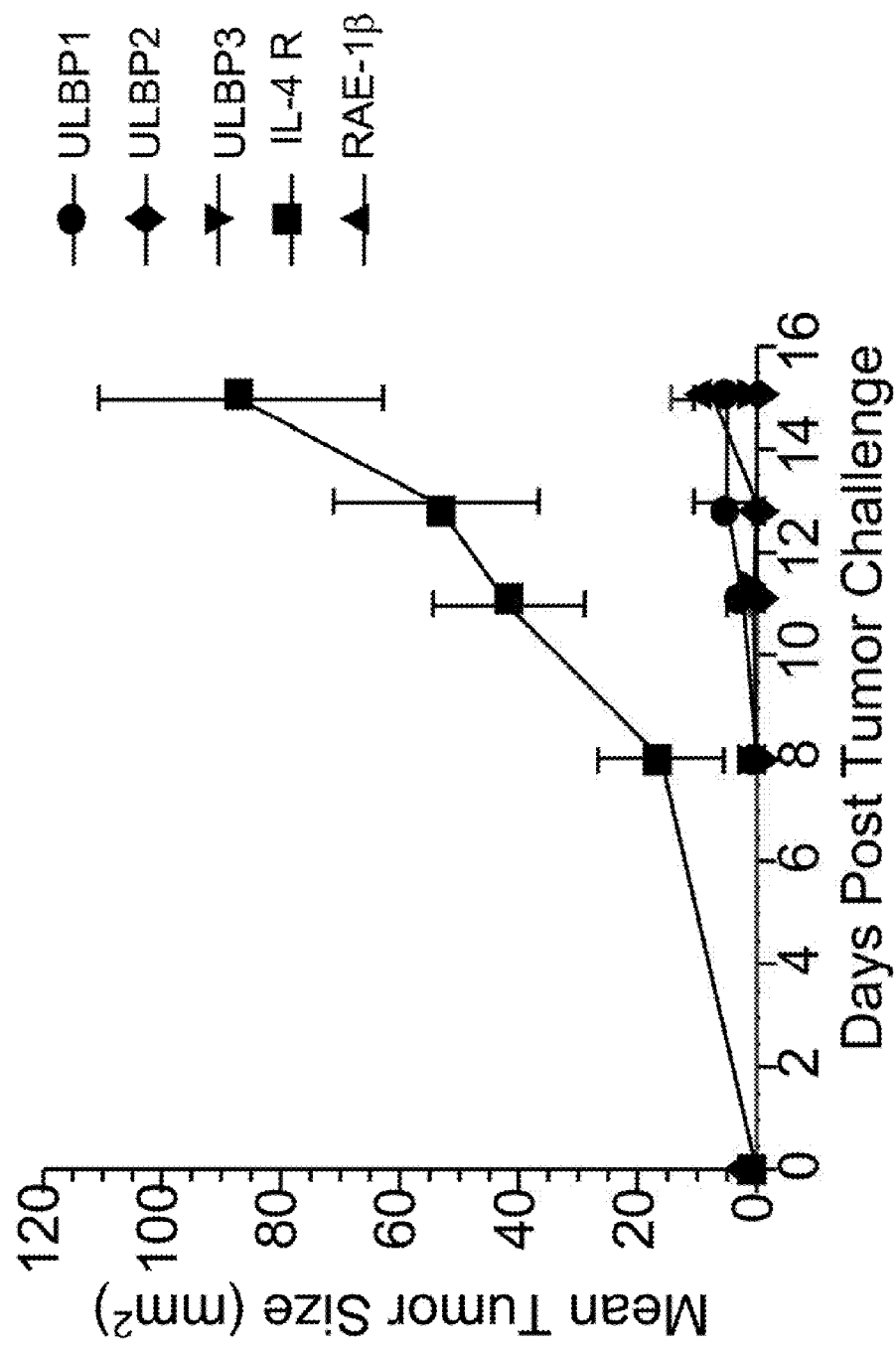
FIG. 3 shows mean tumor size as a function of days post injection of EL4 cells transfected with nucleic acids encoding the indicated proteins into wild type mice.

When injected into mice, EL4 cells can cause tumors. EL4 cells do not express NKG2D ligands. Diefenbach et al. (2000), Nature Immunology 1(2): 119-26. EL4 cells were transfected in culture with either ULBP1, ULBP2, ULBP3, RAE-1β (a murine NKG2D ligand; Diefenbach et al., supra), or a truncated form of murine IL-4 receptor (IL-4R). IL-4 R was not expected to mediate tumor rejection iii vivo and was intended as a negative control. On day zero, $3\times10^5$ EL4 tumor cells expressing either ULBP1, ULBP2, ULBP3, RAE-1β, or IL-4 R were injected subcutaneously into C57/B6 mice. Tumor size was measured over a period of 15-days. Tumor incidence on day 15 is shown in Table 6. Mean tumor size is graphed versus time in FIG. 3.

TABLE 6

| Gene transacted into EL4 cells | Tumor incidence (number of mice having tumors/ total number of injected mice) |
|---|---|
| IL-4 R | 6/6 |
| ULBP1 | 1/7 |
| UBLP2 | 0/6 |
| ULBP3 | 0/7 |
| RAE-1β | 1/7 |

These data indicate that tumors in mice comprising cells expressing ULBPs or RAE-1β are preferentially rejected in vivo when compared to tumors that do not express these NKG2D ligands.

Example 7

ULBP-Mediated Rejection of Tumors in scid Mice In Vivo

The following experiment was designed to determine whether the tumor rejection observed in Example 6 above is dependent on the action of B and/or T cells.

Figure 4:
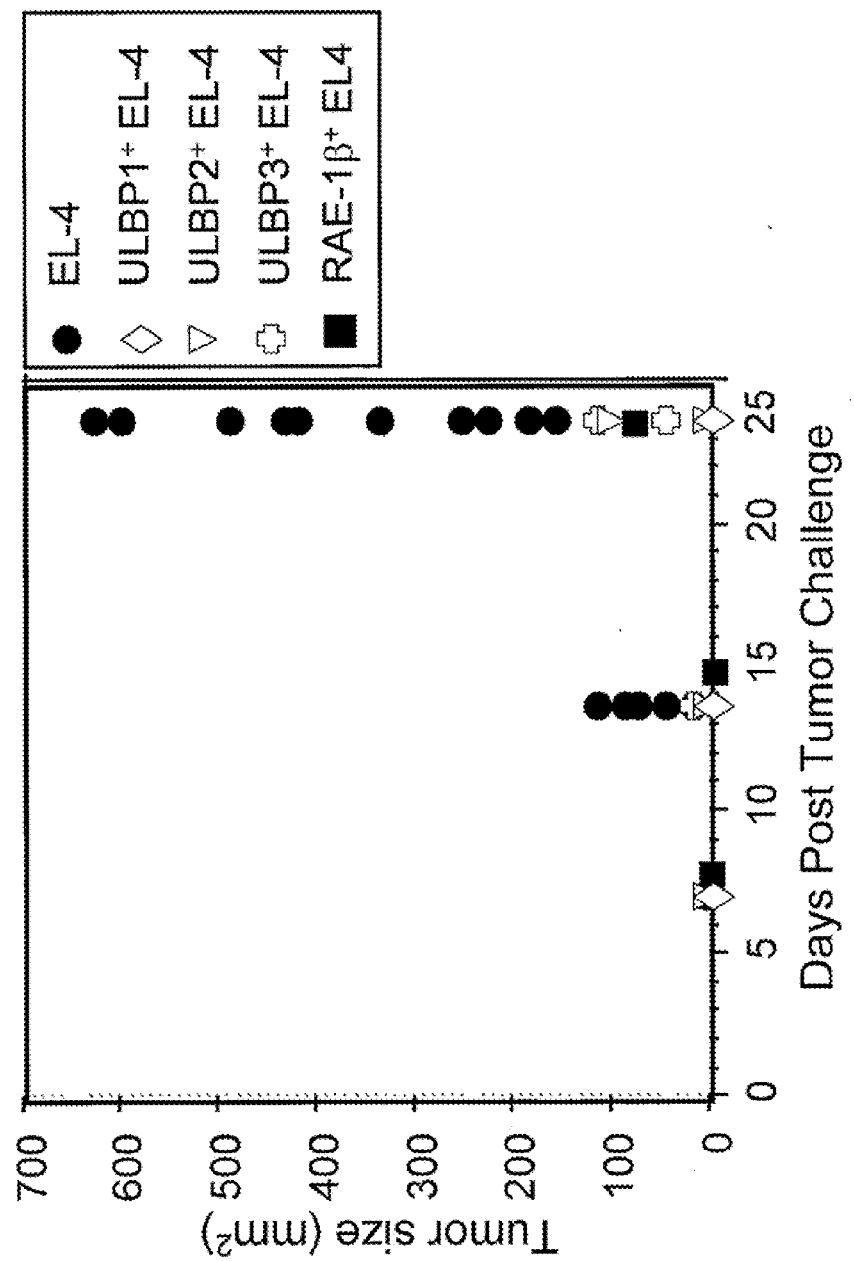
FIG. 4 shows tumor size as a function of days post injection of either untransfected EL4 cells or EL4 cells transfected with nucleic acids encoding the indicated proteins into scid mice.

About 3×10[5] EL4 cells, either not transfected or transfected with either ULBP1, ULBP2, ULBP3, or RAE-1β, were injected into C57/B6 mice bearing a mutation conferring severe combined immune deficiency (scid mice). Ten mice were injected with each kind of cells. Scid mice exhibit a failure of DNA rearrangement in developing lymphocytes and have very few mature B and T cells. Janeway et al., Immunobiology, 5th edition, Part V, Garland Publishing, New York and London (2001). Tumor size was measured on days 1 to 24 and is graphed versus time in FIG. 4. These data indicate that tumor rejection that is dependent upon transfection with RAE-1β or a ULBP occurs in scid mice as well as wild type mice. Thus, such tumor rejection is not likely to depend on the action of B and/or T cells.

The invention has been described with reference to specific examples. These examples are not meant to limit the invention in any way. It is understood for purposes of this disclosure, that various changes and modifications may be made to the invention that are well within the scope of the invention. Numerous other changes may be made which will readily suggest themselves to those skilled in the art and which are encompassed in the spirit of the invention disclosed herein and as defined in the appended claims.

This specification contains numerous citations to patents, patent applications, and publications. Each is hereby incorporated by reference for all purposes.

What is claimed is:

1. An isolated ULBP4 polynucleotide comprising nucleic acid sequence at least 95% identical to SEQ ID NO:1, wherein the nucleic acid sequence encodes a polypeptide that can bind to NKG2D and can stimulate NK cell cytotoxicity.

2. The ULBP4 polynucleotide of claim 1, wherein the polypeptide comprises an alpha-1 domain and an alpha-2 domain.

3. The ULBP4 polynucleotide of claim 1, wherein the nucleotide sequence is at least 97% identical to SEQ ID NO:1.

4. The ULBP4 polynucleotide of claim 1, wherein the polynucleotide further comprises a nucleic acid sequence encoding a heterologous peptide.

5. A vector comprising the ULBP4 polynucleotide of claim 1.

6. An isolated host cell containing the vector of claim 5.

* * * * *